US012667557B2

(12) United States Patent
Yonesaka et al.

(10) Patent No.: US 12,667,557 B2
(45) Date of Patent: Jun. 30, 2026

(54) METHOD FOR TREATING EGFR-TKI-RESISTANT NON-SMALL CELL LUNG CANCER BY ADMINISTRATION OF ANTI-HER3 ANTIBODY-DRUG CONJUGATE

(71) Applicant: DAIICHI SANKYO COMPANY, LIMITED, Tokyo (JP)

(72) Inventors: Kimio Yonesaka, Osaka-Sayama (JP); Kazuhiko Nakagawa, Osaka-Sayama (JP); Kenji Hirotani, Tokyo (JP)

(73) Assignee: DAIICHI SANKYO COMPANY, LIMITED, Tokyo (JP)

( * ) Notice: Subject to any disclaimer, the term of this patent is extended or adjusted under 35 U.S.C. 154(b) by 963 days.

(21) Appl. No.: 16/485,777

(22) PCT Filed: Feb. 27, 2018

(86) PCT No.: PCT/JP2018/007152
§ 371 (c)(1),
(2) Date: Aug. 13, 2019

(87) PCT Pub. No.: WO2018/159582
PCT Pub. Date: Sep. 7, 2018

(65) Prior Publication Data

US 2020/0061031 A1 Feb. 27, 2020

(30) Foreign Application Priority Data

Feb. 28, 2017 (JP) ................................ 2017-035919
Oct. 13, 2017 (JP) ................................ 2017-199883

(51) Int. Cl.
*A61K 31/436* (2006.01)
*A61K 31/506* (2006.01)
(Continued)

(52) U.S. Cl.
CPC .......... *A61K 31/436* (2013.01); *A61K 31/506* (2013.01); *A61K 31/517* (2013.01);
(Continued)

(58) Field of Classification Search
CPC .. A61K 31/436; A61K 31/506; A61K 31/517; A61K 31/535; A61K 31/444;
(Continued)

(56) References Cited

U.S. PATENT DOCUMENTS 5,480,968 A 1/1996 Kraus et al.
5,834,476 A 11/1998 Terasawa et al.
(Continued)

FOREIGN PATENT DOCUMENTS

CA 2927832 A1 11/2011
CA 2815154 2/2012
(Continued)

OTHER PUBLICATIONS

Van Der Steen, N., et al (2016) New developments in the management of non-small-cell lung cancer, focus on rociletinib: what went wrong? OncoTargets and Therapy 9; 6065-6074. (Year: 2016).*
(Continued)

*Primary Examiner* — Scarlett Y Goon
*Assistant Examiner* — Audrey L Buttice
(74) *Attorney, Agent, or Firm* — Foley & Lardner LLP

(57) ABSTRACT

[Problem] To provide a therapeutic agent and a therapeutic method for EGFR-TKI-resistant non-small cell lung cancer. [Solution] Provided are: a therapeutic agent that contains an anti-HER3 antibody-drug conjugate as an active ingredient, or a therapeutic method characterized by administering an anti-HER3 antibody-drug conjugate.

21 Claims, 5 Drawing Sheets

Specification includes a Sequence Listing.

ANTITUMOR EFFECT OF COMBINATION OF HER3-ADC (1) AND OSIMERTINIB ON CELL STRAIN PC9AZDR7 TRANSPLANTED IN NUDE MICE

(51) Int. Cl.

| | |
|---|---|
| ***A61K 31/517*** | (2006.01) |
| ***A61K 31/535*** | (2006.01) |
| ***A61K 45/00*** | (2006.01) |
| ***A61K 47/68*** | (2017.01) |
| ***A61P 11/00*** | (2006.01) |
| ***A61P 35/00*** | (2006.01) |
| ***C07K 16/32*** | (2006.01) |

(52) U.S. Cl.
CPC ............ *A61K 31/535* (2013.01); *C07K 16/32* (2013.01); *A61K 45/00* (2013.01); *A61K 47/68* (2017.08); *A61P 11/00* (2018.01); *A61P 35/00* (2018.01)

(58) Field of Classification Search
CPC .... A61K 31/5377; A61K 45/00; A61K 45/06; A61K 47/68; A61K 47/6857; A61K 47/6803; A61K 2039/505; A61K 2039/55; A61K 2039/86; A61K 39/39558; A61K 39/395; A61K 2300/00; C07K 16/32; C07K 2317/73; C07K 2319/33; A61P 11/00; A61P 35/00
See application file for complete search history.

(56) References Cited

U.S. PATENT DOCUMENTS

| | | | |
|---|---|---|---|
| 5,837,673 | A | 11/1998 | Tsujihara et al. |
| 5,892,043 | A | 4/1999 | Tsujihara et al. |
| 5,968,511 | A | 10/1999 | Akita et al. |
| 6,214,345 | B1 | 4/2001 | Firestone et al. |
| 6,291,671 | B1 | 9/2001 | Inoue et al. |
| 6,835,807 | B1 | 12/2004 | Susaki et al. |
| 7,585,491 | B2 | 9/2009 | Govindan |
| 7,837,980 | B2 | 11/2010 | Alley et al. |
| 2003/0148931 | A1 | 8/2003 | Takahashi et al. |
| 2003/0166513 | A1 | 9/2003 | Imura et al. |
| 2004/0185053 | A1 | 9/2004 | Govindan |
| 2005/0123536 | A1 | 6/2005 | Law et al. |
| 2005/0271671 | A1 | 12/2005 | Griffiths |
| 2005/0276812 | A1 | 12/2005 | Ebens, Jr. et al. |
| 2006/0092230 | A1 | 5/2006 | Steiner et al. |
| 2006/0193865 | A1 | 8/2006 | Govindan |
| 2007/0071764 | A1 | 3/2007 | Sullivan et al. |
| 2008/0050310 | A1 | 2/2008 | Ebens et al. |
| 2008/0124345 | A1 | 5/2008 | Rothe et al. |
| 2008/0131363 | A1 | 6/2008 | Govindan et al. |
| 2008/0161245 | A1 | 7/2008 | Kratz et al. |
| 2008/0305044 | A1 | 12/2008 | Mcdonagh et al. |
| 2009/0274713 | A1 | 11/2009 | Chari et al. |
| 2010/0183631 | A1 | 7/2010 | Rothe et al. |
| 2010/0196265 | A1 | 8/2010 | Adams et al. |
| 2011/0070248 | A1 | 3/2011 | Ichikawa et al. |
| 2011/0123523 | A1 | 5/2011 | Schoeberl et al. |
| 2011/0229406 | A1 | 9/2011 | Hettmann et al. |
| 2011/0293513 | A1 | 12/2011 | Govindan et al. |
| 2012/0058122 | A1 | 3/2012 | Rothe et al. |
| 2012/0121615 | A1 | 5/2012 | Flygare et al. |
| 2012/0201809 | A1 | 8/2012 | Bhat et al. |
| 2013/0123178 | A1 | 5/2013 | Dimarchi et al. |
| 2014/0017166 | A1 | 1/2014 | Hettmann et al. |
| 2014/0314774 | A1 | 10/2014 | Zhou et al. |
| 2014/0363429 | A1 | 12/2014 | Chowdhury et al. |
| 2015/0086478 | A1 | 3/2015 | Lantto et al. |
| 2015/0297748 | A1 | 10/2015 | Masuda et al. |
| 2015/0352224 | A1 | 12/2015 | Naito et al. |
| 2016/0159913 | A1 | 6/2016 | Chowdhury et al. |
| 2016/0168264 | A1 | 6/2016 | Rothe et al. |
| 2016/0222126 | A1 | 8/2016 | Hettmann et al. |
| 2016/0237162 | A1 | 8/2016 | Chowdhury et al. |
| 2016/0287722 | A1 | 10/2016 | Govindan |
| 2016/0333112 | A1 | 11/2016 | Naito et al. |
| 2017/0021031 | A1 | 1/2017 | Hettmann et al. |
| 2017/0165365 | A1 | 6/2017 | Lantto et al. |
| 2017/0233490 | A1 | 8/2017 | Bossenmaier et al. |
| 2017/0240648 | A1 | 8/2017 | Schlessinger et al. |
| 2017/0306049 | A1 | 10/2017 | Yarden et al. |
| 2018/0134805 | A1 | 5/2018 | Hettmann et al. |
| 2018/0155433 | A1 | 6/2018 | Chard et al. |
| 2018/0193477 | A1 | 7/2018 | Ng et al. |
| 2018/0344846 | A1 | 12/2018 | Lantto et al. |
| 2019/0040143 | A1 | 2/2019 | Chowdhury et al. |
| 2019/0077880 | A1 | 3/2019 | Naito et al. |
| 2019/0151328 | A1 | 5/2019 | Hettmann et al. |
| 2019/0263930 | A1 | 8/2019 | Rothe et al. |
| 2020/0385486 | A1 | 12/2020 | Naito et al. |
| 2022/0172420 | A1 | 6/2022 | Hettmann et al. |

FOREIGN PATENT DOCUMENTS

| | | | |
|---|---|---|---|
| CA | 2859255 | A1 | 6/2013 |
| CN | 1227499 | A | 9/1999 |
| CN | 1764478 | A | 4/2006 |
| CN | 101490087 | A | 7/2009 |
| CN | 105829346 | A | 8/2016 |
| CN | 106163559 | A | 11/2016 |
| EP | 0 495 432 | A1 | 7/1992 |
| EP | 0 737 686 | A1 | 10/1996 |
| EP | 0 916 348 | A1 | 5/1999 |
| EP | 1 155 702 | A1 | 11/2001 |
| EP | 2 907 824 | A1 | 8/2015 |
| JP | H05-059061 | A | 3/1993 |
| JP | H08-337584 | A | 12/1996 |
| JP | H10-095802 | A | 4/1998 |
| JP | H1171280 | A | 3/1999 |
| JP | H11-092405 | A | 4/1999 |
| JP | 2002-060351 | A | 2/2002 |
| JP | 2005-511627 | A | 4/2005 |
| JP | 2006-511526 | A | 4/2006 |
| JP | 2008-521828 | A | 6/2008 |
| JP | 2009-538629 | A | 11/2009 |
| JP | 2012-100671 | A | 5/2012 |
| JP | 2013-534535 | A | 9/2012 |
| JP | 2013-534906 | A | 9/2013 |
| JP | 2017-503784 | A | 2/2017 |
| KR | 1020010052385 | A | 6/2001 |
| KR | 1020110044808 | A | 4/2011 |
| KR | 1020160144396 | A | 12/2016 |
| RU | 2404810 | C2 | 11/2010 |
| TW | 1232930 | | 5/2005 |
| TW | 200817434 | A | 4/2008 |
| TW | 201542230 | | 11/2015 |
| WO | WO-97/46260 | A1 | 12/1997 |
| WO | WO-00/25825 | A1 | 5/2000 |
| WO | WO-02/00734 | A1 | 1/2002 |
| WO | WO-03/013602 | A1 | 2/2003 |
| WO | WO-03/043583 | A2 | 5/2003 |
| WO | WO-2005/112919 | A2 | 12/2005 |
| WO | WO-2006/065533 | A2 | 6/2006 |
| WO | WO-2006/092230 | A2 | 9/2006 |
| WO | WO-2007/077028 | A2 | 7/2007 |
| WO | WO-2007/100385 | A2 | 9/2007 |
| WO | WO-2008/100624 | A2 | 8/2008 |
| WO | WO-2008/140493 | A2 | 11/2008 |
| WO | WO-2011/011474 | A1 | 1/2011 |
| WO | WO-2011/060206 | A2 | 5/2011 |
| WO | WO-2011/068845 | A1 | 6/2011 |
| WO | WO-2012/019024 | A2 | 2/2012 |
| WO | WO-2012/064733 | A2 | 5/2012 |
| WO | WO-2013/071058 | A1 | 5/2013 |
| WO | WO-2013/078191 | A1 | 5/2013 |
| WO | WO-2013/163229 | A1 | 10/2013 |
| WO | WO-2013/164689 | A2 | 11/2013 |
| WO | WO-2013/188740 | A1 | 12/2013 |
| WO | WO-2014/057687 | A1 | 4/2014 |
| WO | WO-2014/061277 | A1 | 4/2014 |
| WO | WO-2014/107024 | A1 | 7/2014 |
| WO | WO-2015/048008 | A2 | 4/2015 |
| WO | WO-2015/155998 | A1 | 10/2015 |
| WO | WO-2015/157634 | A1 | 10/2015 |
| WO | WO-2015/173248 | A1 | 11/2015 |

(56) References Cited

FOREIGN PATENT DOCUMENTS

WO WO-2016/038609 A1 3/2016
WO WO-2016/177664 A1 11/2016
WO WO-2017/008169 A1 1/2017

OTHER PUBLICATIONS

Tetsu, O., et al (2015) Drug Resistance to EGFR Inhibitors in Lung Cancer Chemotherapy 16(61); 223-235 (Year: 2015).*
Tang, Z.H., et al (2016) Characterization of osimertinib (AZD9291)-resistant non-small cell lung cancer NCI-H1975/OSIR cell line Oncotarget 7(49); 81598-81610 (Year: 2016).*
Byeon et al., (2019) Beyond EGFR inhibition: multilateral combat strategies to stop the progression of head and neck cancer Experimental & Molecular medicine, 51(8); 1-14 (Year: 2019).*
Office Action dated Aug. 27, 2020 for corresponding Canadian Patent Application No. 3053749.
Office Action dated Sep. 18, 2020 for corresponding Singapore Patent Application No. 11201907050P.
Acchione et al., Impact of linker and conjugation chemistry on antigen binding, Fc receptor binding and thermal stability of model antibody-drug conjugates, mAbs, 2012, pp. 362-372—(12 pages).
Alimandi et al., "Cooperative signaling of ErbB3 and ErbB2 in neoplastic transformation and human mammary carcinomas," Oncogene 10:1813-1821 (1995)—9 Pages.
Alley et al., "Antibody-drug conjugates: targeted drug delivery for cancer," Current Opinion in Chemical Biology 14:529-537 (2010)—9 Pages.
Barginear et al., "Trastuzumab-DM1: A Review of the Novel Immuno-Conjugate for HER2-Overexpressing Breast Cancer," The Open Breast Cancer Journal 1:25-30 (2009).
Barok et al., Trastuzumab-DM1 is highly effective in preclinical models of HER2-positive gastric cancer, Cancer Letters, 2011, vol. 306, No. 2, pp. 172-179 (9 pages).
Beck, Alain, "The Next Generation of Antibody-drug Conjugates Comes of Age," Discovery Medicine 10(53):329-339 (Oct. 16, 2010)—8 Pages.
BURKE P J et al. (2009), "Design, Synthesis, and Biological Evaluation of Antibody-Drug Conjugates Comprised of Potent Camptothecin Analogues", Bioconjugate Chemistry, vol. 20, No. 6, pp. 1242-1250—9 Pages.
Canadian Office Action dated Apr. 13, 2018 in corresponding application No. 2939802.
Chinese Office Action dated Nov. 1, 2016 in corresponding application No. 201380053256.2.
Chinese Office Action dated Nov. 8, 2019 for corresponding Application No. 201580019138.9—4 pages.
Chinese Office Action issued to corresponding App. No. 201480071134.0—DTD Aug. 20, 2019 (5 pages).
Colombian Reconsideration Petition dated Mar. 15, 2018 in corresponding application No. NC2016/0000187—36 pages.
Conjugation site modulates the in vivo stability and therapeutic activity of antibody-drug conjugates, Shen et al., Nature Biotechnology, 2012, vol. 30, pp. 184-189.
Damle, Nitin K., "Tumour-targeted chemotherapy with immunoconjugates of calicheamicin," Expert Opin. Biol. Ther. 4(9):1445-1452 (2004)—8 Pages.
De Jager et al., "DX-8951f: Summary of Phase I Clinical Trials," Ann. N.Y. Acad. Sci. 922:260-273 (2000)—16 Pages.
Defazio et al., "Expression of c-erbB Receptors, Heregulin and Oestrogen Receptor in Human Breast Cell Lines," Int. J. Cancer 87:487-498 (2000)—12 Pages.
Ducry et al., "Antibody-Drug Conjugates: Linking Cytotoxic Payloads to Monoclonal Antibodies," Bioconjugate Chem. 21:5-13 (2010)—9 Pages.
English-language translation of International Search Report issued in International Patent Application No. PCT/JP2015/002020 mailed Jul. 20, 2015—4 Pages.
European Search Report issued in corresponding U.S. Appl. No. 14/874,745 dated May 10, 2017.
Extended European Search Report issued in European Patent Application No. 15743738.5 dated Aug. 9, 2017.
Extended European Search Report issued in European Patent Application No. 15776810.2 dated Aug. 11, 2017.
Inoue et al., "CM-Dextran-Polyalcohol-Camptothecin Conjugate: DE-310 with A Novel Carrier System and Its Preclinical Data," Polymer Drugs in the Clinical Stage, 145-153 (2003)—9 Pages.
Interview Summary Acknowledgement in Canada Application No. 2885800 dated Mar. 28, 2017.
Japanese Notice Of Allowance dated Oct. 18, 2016 in corresponding application No. 2016-166850.
Japanese Office Action dated Dec. 6, 2016 in corresponding application No. 2016-540705.
Joto et al., "DX-8951F, A Water-Soluble Camptothecin Analog, Exhibits Potent Antitumor Activity Against a Human Lung Cancer Cell Line and its SN-38-Resistant Variant," Int. J. Cancer 72:680-686 (1997)—7 Pages.
Kang et al., Engineering multivalent antibodies to target heregulin-induced HER3 signaling in breast cancer cells, mAbs, Mar./Apr. 2014, vol. 6, No. 2, pp. 340-353.
Kawakami et al—"The anti-HER3 antibody patritumab abrogates cetuximab resistance mediated by heregulin in colorectal cancer cells", Oncotarget, vol. 5, No. 23, Dec. 5, 2014, 11847-11856—10 pages.
Korean Office Action dated May 1, 2018 in corresponding application No. 10-2016-7015961.
Kraus et al., "Demonstration of ligand-dependent signaling by the erbB-3 tyrosine kinase and its constitutive activation in human breast tumor cells," Proc. Natl. Acad. Sci. USA 90:2900-2904 (Apr. 1993)—5 Pages.
Kraus et al., "Isolation and characterization of ERBB3, a third member of the ERBB/epidermal growth factor receptor family: Evidence for overexpression in a subset of human mammary tumors," Proc. Natl. Acad. Sci. USA 86:9193-9197 (Dec. 1989)—5 pages.
Kumazawa et al., "Antitumor activity of DX-8951f: a new camptothecin derivative," Exp. Opin. Invest. Drugs 7(4):625-632 (1998)—8 Pages.
Kumazawa et al., "DE-310, a novel macromolecular carrier system for the camptothecin analog DX-8951f: Potent antitumor activities in various murine tumor models," Cancer Sci. 95(2):168-175 (Feb. 2004)—8 Pages.
Kumazawa et al., "Potent and broad antitumor effects of DX-8951f, a water-soluble camptothecin derivative, against various human tumors xenografted in nude mice," Cancer Chemother. Pharmacol. 42:210-220 (1998)—11 Pages.
Methods for site-specific drug conjugation to antibodies, Behrens et al., mAbs, 2014, vol. 6, No. 1, pp. 46-53.
Mitsui et al., "A New Water-soluble Camptothecin Derivative, DX-8951f, Exhibits Potent Antitumor Activity against Human Tumors in vitro and in vivo," Jpn. J. Cancer Res. 86:776-782 (Aug. 1995)—7 Pages.
N. Masucuchi, "Pharmacokinetics of DE-310, a novel macromolecular carrier system for the camptothecin analog DX-8951f, in tumor-bearing mice," Pharmazie 59: 374-377 (2004).
Naidu et al., "Expression of c-erbB3 protein in primary breast carcinomas," British Journal of Cancer 78(10): 1385-1390 (1998)—6 Pages.
Nakada et al., "Novel antibody drug conjugates containing exatecan derivative-based cytotoxic payloads," Bioorganic & Medical Chemistry Letters 26(6): 1542-1545 (2016)—4 Pages.
Office Action issued in Chinese Application No. 201380053256.2 dated Nov. 1, 2016—12 Pages.
Office Action issued in Colombian Application No. NC2016/0000187 mailed on May 9, 2017. An English translation is provided.
Office Action issued in Japanese Application No. 2016-540705 dated Dec. 6, 2016—2 Pages.
Oguma et al, Validation study of a method for assaying DE-310, a macromolecular carrier conjugate containing an anti-tumor camptothecin derivative, and the free drug in tumor tissue by high performance

(56) References Cited

OTHER PUBLICATIONS liquid chromatography/atmospheric pressure chemical ionization tandem mass spectrometry, Biomedical Chromatography, 2005, vol. 19, No. 1, pp. 19-26—(8 pages).
Otto Soepenberg, "chromatographic assays for DE-310, a novel camptothecin analog, and two major enzymatic products in human matrices," Journal of Chromatography B, 799, 15-22 (2004).
Plowman et al., "Molecular cloning and expression of an additional epidermal growth factor receptor-related gene," Proc. Natl. Acad. Sci. USA 87:4905-4909 (Jul. 1990)—5 Pages.
Rowinsky, Preclinical and Clinical Development of Exatecan(DX-8951f), Camptothecins in Cancer Therapy, 2005, pp. 317-318 (25 pages).
Russian Office Action dated Mar. 5, 2019 in corresponding application No. 2016143351.
Russian Office Action dated Oct. 11, 2018 in corresponding application No. 2016123597—13 pages.
Senter et al., "The discovery and development of brentuximab vedotin for use in relapsed Hodgkin lymphoma and systemic anaplastic large cell lymphoma," Nature Biotechnology 30(7):631-637 (Jul. 2012)—7 Pages.
Shiose et al, "Systematic Research of Peptide Spacers Controlling Drug Release from Macromolecular Prodrug System, Carboxymethyldextran Polyalcohol-Peptide-Drug Conjugates," Bioconjugate Chem. 20(1):60-70(2009).
Sievers et al, Antibody-Drug Conjugates in Cancer Therapy, Annual Review of Medicine, 2013, vol. 64, No. 1, pp. 15-29.
Soepenberg et al., "Phase I and Pharmacokinetic Study of DE-310 in Patients with Advanced Solid Tumors," Clin. Cancer Res. 11:703-711 (Jan. 15, 2005)—9 Pages.
Taiwanese Office Action dated Jul. 30, 2018 in corresponding application No. 104111534.
Taiwanese Office Action dated May 15, 2017 in corresponding application No. 102136742.
Takiguchi et al., "Antitumor Effect of DX-8951, a Novel Camptothecin Analog, on Human Pancreatic Tumor Cells and Their CPT-11-resistant Variants Cultured in vitro and Xeografted in Nude Mice," Jpn. J. Cancer Res. 88:760-769 (Aug. 1997)—10 Pages.
Thomas M. Cardillo, "Humanized Anti-Trop-2 IgG-SN-38 Conjugate for Effective Treatment of Diverse Epithelial Cancers: Preclinical Studies in Human Cancer Xenograft Models and Monkeys," Clinical Cancer Research 17(10): 3157-3169 (2011).
Wente et al., "DE-310, a macromolecular prodrug of the topoisomerase-I-inhibitor exatecan (DX-8951), in patients with operable solid tumors," Investigational New Drugs 23:339-347 (2005)—9 Pages.
Yusuke Ochi, "Possible Mechanism for the long-lasting antitumor effect of the macromolecular conjugate DE-310: mediation by cellular uptake and drug release of its active camptothecin analog DX-8951," Cancer Chemother Pharmacol (2005) 55: 323-332.
Kimio Yonesaka, "Anti-HER3 Antibody Patritumab Overcomes Resistance to EGFR Inhibitor in Non-small Cell Lung Cancer", The Japan Lung Cancer Society, vol. 55, pp. 948-955, 2015 (8 pages).
P. Janne, et al., "Phase 1 study of the Anti-HER3 Antibody Drug Conjugate U3-1402 in Metastic or Unresectable EGFR-mutant NSCLC.", Journal of Thoracic Oncology, vol. 12, No. 11, Supp. Supplement 2, pp. S2290, abstract No. P3.04-013, Nov. 2017 (3 pages).
I. Sullivan, et al. "Osimertinib in the treatment of patients with epidermal growth factor receptor T790M mutation-positive metastatic non-small cell lung cancer: clinical trial evidence and experience", Therapeutic Advances in Respiratory Disease, vol. 10(6), pp. 549-565, 2016 (17 pages).
N.V. Sergina, et al. "Escape from HER-family tyrosine kinase inhibitor therapy by the kinase-inactive HER3", Nature, vol. 445, pp. 437-441, 2007 (6 pages).
K. Yonesaka, et al., "Anti-HER3 monoclonal antibody patritumab sensitizes refractory non-small cell lung cancer to the epidermal growth factor receptor inhibitor erlotinib", Oncogene vol. 35, pp. 878-886, 2016 (10 pages).
Howard A., et al., " Phase II Study of the Antibody Drug Conjugate Trastuzumab-DM1 for the Treatment of Human Epidermal Growth Factor Receptor 2 (HER2)-Positive Breast Cancer After Prior HER2-Directed Therapy", Journal of Clinical Oncology, vol. 29, pp. 398-405, 2011 (8 pages).
International Search Report and Written Opinion for correspondence Application No. PCT/JP2018/007152 dated Apr. 24, 2018.
Extended European Search Report dated Nov. 19, 2020 for corresponding European Patent Application No. 18760248.7.
Gianluca Sala et al, "EV20, a Novel Anti-ErbB-3 Humanized Antibody, Promotes ErbB-3 Down-Regulation and Inhibits Tumor Growth in Vivo", Translational Oncology 2013, vol. 6, pp. 676-684.
Jian Ma et al, "Targeting of erbB3 receptor to overcome resistance in cancer treatment", Molecular Cancer 2014, vol. 13, p. 105.
Examination Report dated Feb. 10, 2022 for corresponding Indian Patent Application No. 201917033140.
Office Action dated Dec. 30, 2021 for corresponding Singapore Patent Application No. 11201907050P.
Non-Final Office Action dated Apr. 5, 2019 in U.S. Appl. No. 15/821,697.
Notice of Reasons for Rejection issued in corresponding Japanese Patent Application No. 2019-503002 dated Feb. 8, 2022.
Office Action dated Nov. 29, 2021 issued in a corresponding Indian Patent Application No. 202018030127, (7 pages).
Office Action issued in U.S. Appl. No. 15/187,179 dated Oct. 21, 2016.
Tian, et al., "A general approach to site-specific antibody drug conjugates", Proceedings of the National Academy of Sciences 111(5):1766-1771 (2014).
Taiwan Office Action issued in connection with TW Appl. Ser. No. 107106568 dated May 9, 2022 (11 pages).
Office Action issued in corresponding Japanese Patent Application No. 2019-503002, dated Jul. 5, 2022.
Chinese Office Action issued in connection with CN Appl. Ser. No. 201880014522.3 dated Sep. 21, 2022.
Office Action issued in corresponding European U.S. Appl. No. 18/760,248, dated Aug. 19, 2022.
Park Mi-Young et al: "Generation of lung cancer cell lines harboring EGFR T790M mutation by CRISPR/Cas9-mediated genome editing", Oncotarget, vol. 8, No. 22, May 30, 2017 (May 30, 2017), pp. 36331-36338, XP055951504, DOI: 10.18632/oncotarget.16752.
Pasi A Janne et al: "Phase 1 study of the anti-H ER3 antibody drug conjugate U3-1402 in metastatic or unresectable EGFR-mutant NSCLC", Journal of Clinical Oncology, May 20, 2018 (May 20, 2018), pp. TPS911 0-TPS9110, XP055538838, DOI: 10.1200/JCO.2018.36.15_suppl. TPS9110.
Yonesaka Kimio et al: "Heregulin expression and its clinical implication for patients with EGFR-mutant non-small cell lung cancer treated with EGFR-tyrosine kinase inhibitors", Scientific Reports, vol. 9, No. 1, Dec. 1, 2019 (Dec. 1, 2019), XP055951507, DOI: 10.1038/s41598-019-55939-5 Retrieved from the Internet: URL:http://www.nature.com/articles/s41598-019-55939-5.
Office Action, dated Jun. 1, 2023, issued in corresponding Chinese Patent Application No. 201880014522.3 (13 pages).
Office Action, dated Jul. 25, 2023, issued in corresponding Korean Patent Application No. 10-2019-7025656 (15 pages).
Office Action issued in corresponding Korean Patent Application No. 10-2019-7025656 dated Dec. 12, 2023 (10 pages).
Office Action issued in Taiwanese Patent Application No. 107106568, dated Aug. 30, 2022.
Li et al., "Synergistic interaction between MEK inhibitor and gefitinib in EGFR-TKI-resistant human lung cancer cells", Oncol. Lett., vol. 10, No. 4, pp. 2652-2656, Aug. 6, 2015.
Office Action issued in corresponding Canadian Patent Application No. 3,053,749 dated Dec. 13, 2024.
NCT03260491, "U3-1402 in Metastatic or Unresectable Non-Small Cell Lung Cancer", Aug. 22, 2017, Arms and Interventions, National Library of Medicine, Retrieved from: https://clinicaltrials.gov/study/NCT03260491?tab=history&a=1 on May 20, 2024, pp. 1-15.
Office Action issued in corresponding Singaporean Patent Application No. 11201907050P dated Apr. 1, 2024 (9 pages).
Office Action issued in corresponding Japanese Patent Application No. 2022-157622 dated Oct. 3, 2023 (6 pages).

(56) References Cited

OTHER PUBLICATIONS

Office Action issued in corresponding Taiwanese Patent Application No. 107106568 dated Oct. 11, 2023 (20 pages).

* cited by examiner

[Figure 1]

SEQ ID NO:9: AMINO ACID SEQUENCE OF A HEAVY CHAIN OF ANTI-HER3 ANTIBODY (1)

QVQLQQWGAGLLKPSETLSLTCAVYGGSFSGYYWSWIRQPPGKGLEWIGEINHSGSTNYNPSLK
SRVTISVETSKNQFSLKLSSVTAADTAVYYCARDKWTWYFDLWGRGTLVTVSSASTKGPSVFPL
APSSKSTSGGTAALGCLVKDYFPEPVTVSWNSGALTSGVHTFPAVLQSSGLYSLSSVVTVPSSS
LGTQTYICNVNHKPSNTKVDKRVEPKSCDKTHTCPPCPAPELLGGPSVFLFPPKPKDTLMISRT
PEVTCVVVDVSHEDPEVKFNWYVDGVEVHNAKTKPREEQYNSTYRVVSVLTVLHQDWLNGKEYK
CKVSNKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLSLSPGK

[Figure 2]

SEQ ID NO:10: AMINO ACID SEQUENCE OF A LIGHT CHAIN OF ANTI-HER3 ANTIBODY (1)

DIEMTQSPDSLAVSLGERATINCRSSQSVLYSSSNRNYLAWYQQNPGQPPKLLIYWASTRESGV
PDRFSGSGSGTDFTLTISSLQAEDVAVYYCQQYYSTPRTFGQGTKVEIKRTVAAPSVFIFPPSD
EQLKSGTASVVCLLNNFYPREAKVQWKVDNALQSGNSQESVTEQDSKDSTYSLSSTLTLSKADY
EKHKVYACEVTHQGLSSPVTKSFNRGEC

[Figure 3]

CELL PROLIFERATION SUPPRESSING ACTIVITY AGAINST CELL STRAIN HCC827 AND CELL STRAIN HCC827GR5

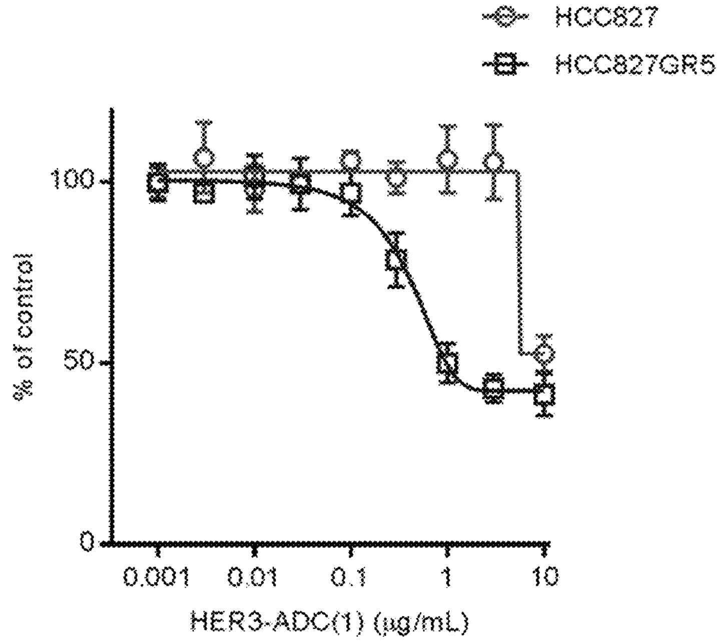

[Figure 4]
HER3 mRNA EXPRESSION LEVELS IN CELL STRAIN HCC827 AND CELL STRAIN HCC827GR5
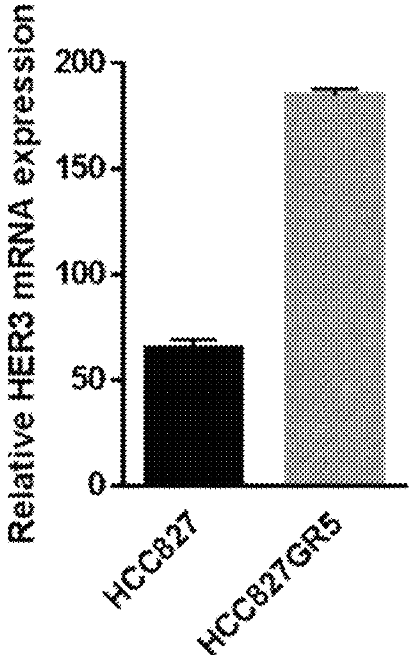
[Figure 5]
CELL PROLIFERATION SUPPRESSING ACTIVITY AGAINST CELL STRAIN HCC827GR5
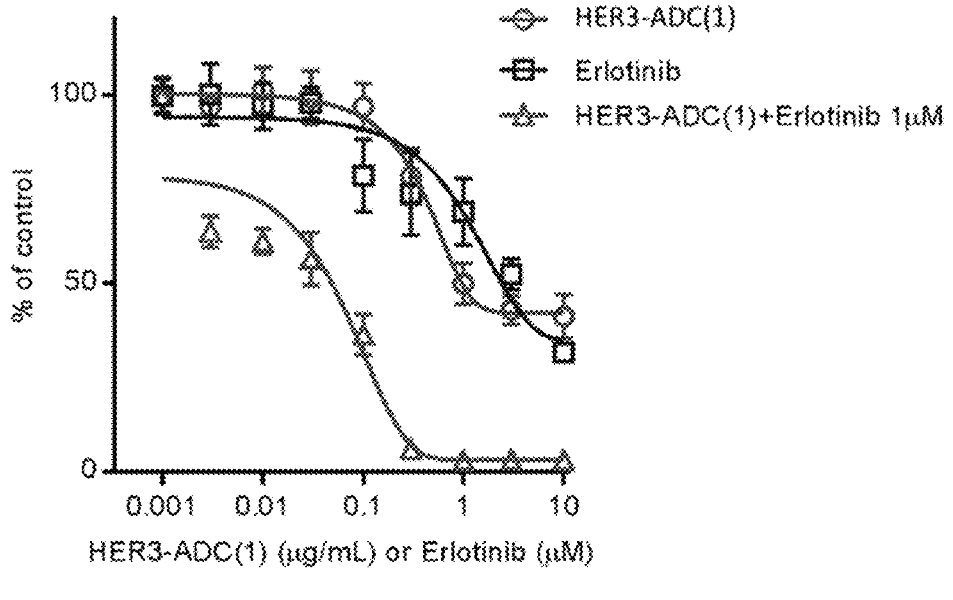

[Figure 6]
ANTITUMOR EFFECT ON CELL STRAIN HCC827GR5 TRANSPLANTED IN NUDE MICE
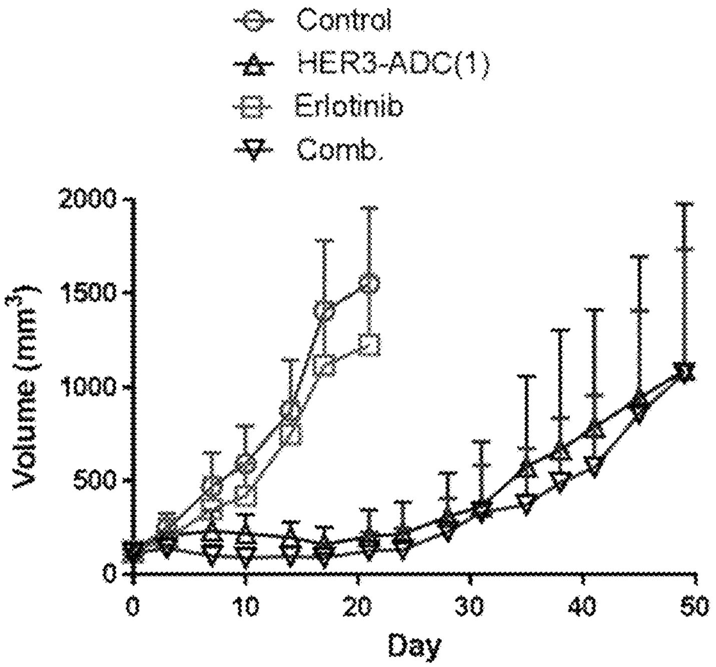
[Figure 7]
CELL PROLIFERATION SUPPRESSING ACTIVITY OF OSIMERTINIB AGAINST CELL STRAIN PC9 AND CELL STRAIN PC9AZDR7
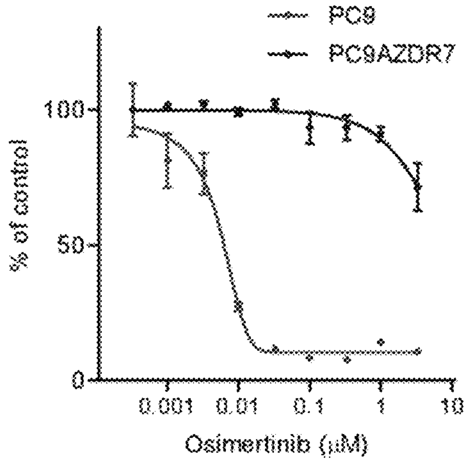

[Figure 8]
HER3 PROTEIN LEVELS IN CELL STRAIN PC9 AND CELL STRAIN PC9AZDR7
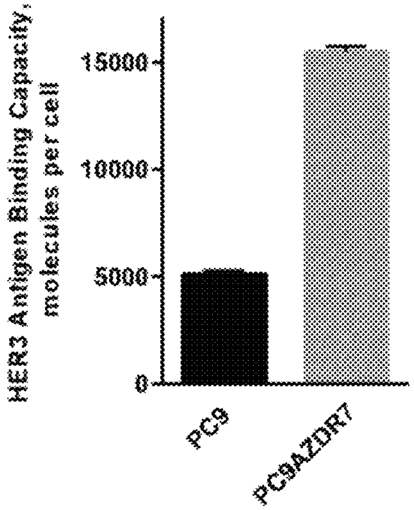
[Figure 9]
ANTITUMOR EFFECT OF HER3-ADC (1) ALONE ON CELL STRAIN PC9 TRANSPLANTED IN NUDE MICE
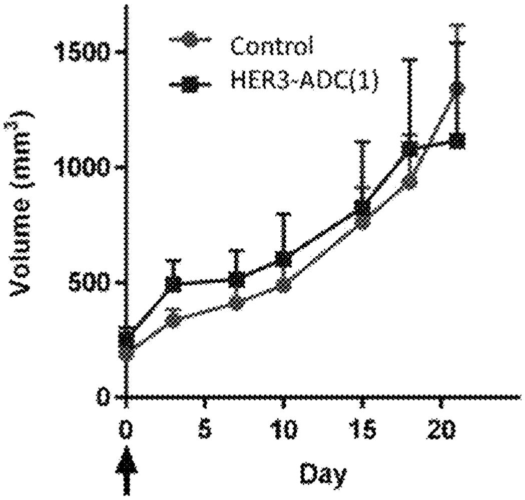

[Figure 10]
ANTITUMOR EFFECT OF HER3-ADC (1) ALONE ON CELL STRAIN PC9AZDR7 TRANSPLANTED IN NUDE MICE
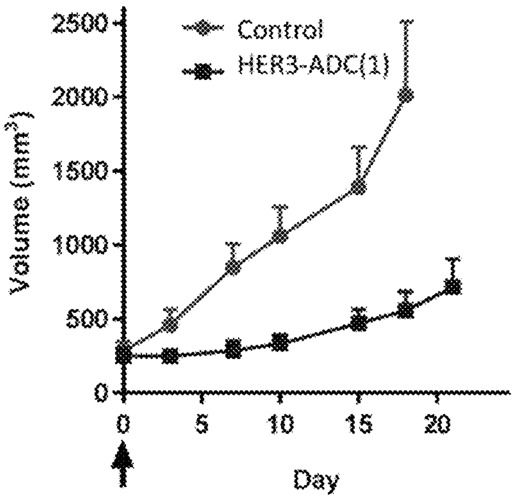
[Figure 11]
ANTITUMOR EFFECT OF COMBINATION OF HER3-ADC (1) AND OSIMERTINIB ON CELL STRAIN PC9AZDR7 TRANSPLANTED IN NUDE MICE
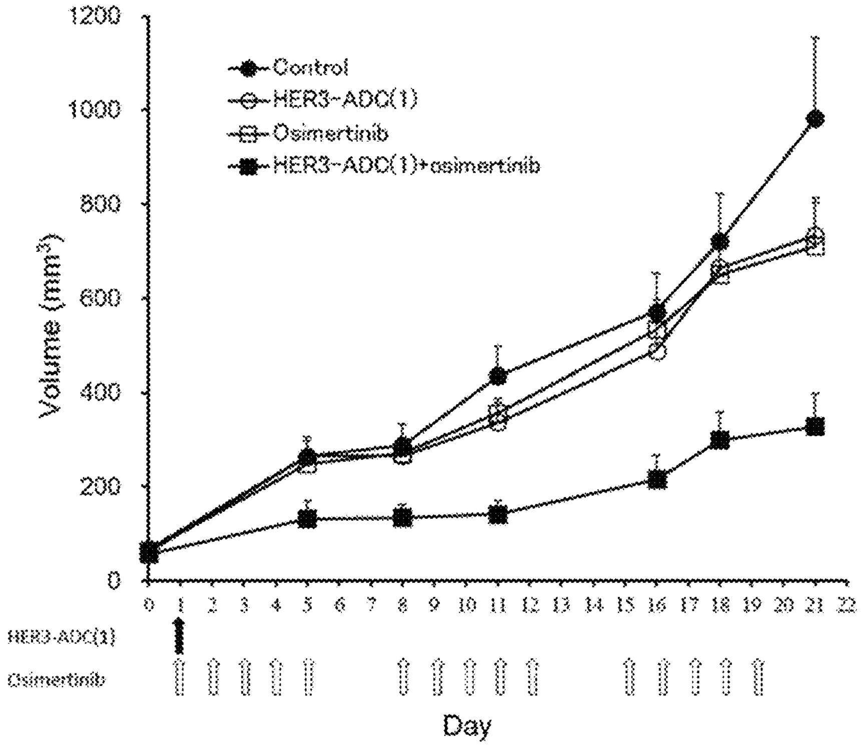

```
                              SEQUENCE LISTING


<160> NUMBER OF SEQ ID NOS: 10

<210> SEQ ID NO 1
<211> LENGTH: 10
<212> TYPE: PRT
<213> ORGANISM: Artificial
<220> FEATURE:
<223> OTHER INFORMATION: anti-HER3 antibody (1) CDRH1

<400> SEQUENCE: 1

Gly Gly Ser Phe Ser Gly Tyr Tyr Trp Ser
1               5                   10


<210> SEQ ID NO 2
<211> LENGTH: 16
<212> TYPE: PRT
<213> ORGANISM: Artificial
<220> FEATURE:
<223> OTHER INFORMATION: anti-HER3 antibody (1) CDRH2

<400> SEQUENCE: 2

Glu Ile Asn His Ser Gly Ser Thr Asn Tyr Asn Pro Ser Leu Lys Ser
1               5                   10                  15


<210> SEQ ID NO 3
<211> LENGTH: 9
<212> TYPE: PRT
<213> ORGANISM: Artificial
<220> FEATURE:
<223> OTHER INFORMATION: anti-HER3 antibody (1) CDRH3

<400> SEQUENCE: 3

Asp Lys Trp Thr Trp Tyr Phe Asp Leu
1               5


<210> SEQ ID NO 4
<211> LENGTH: 17
<212> TYPE: PRT
<213> ORGANISM: Artificial
<220> FEATURE:
<223> OTHER INFORMATION: anti-HER3 antibody (1) CDRL1

<400> SEQUENCE: 4

Arg Ser Ser Gln Ser Val Leu Tyr Ser Ser Ser Asn Arg Asn Tyr Leu
1               5                   10                  15

Ala


<210> SEQ ID NO 5
<211> LENGTH: 7
<212> TYPE: PRT
```

<213> ORGANISM: Artificial
<220> FEATURE:
<223> OTHER INFORMATION: anti-HER3 antibody (1) CDRL2

<400> SEQUENCE: 5

Trp Ala Ser Thr Arg Glu Ser
1               5

<210> SEQ ID NO 6
<211> LENGTH: 9
<212> TYPE: PRT
<213> ORGANISM: Artificial
<220> FEATURE:
<223> OTHER INFORMATION: anti-HER3 antibody (1) CDRL3

<400> SEQUENCE: 6

Gln Gln Tyr Tyr Ser Thr Pro Arg Thr
1               5

<210> SEQ ID NO 7
<211> LENGTH: 117
<212> TYPE: PRT
<213> ORGANISM: Artificial
<220> FEATURE:
<223> OTHER INFORMATION: anti-HER3 antibody (1) VH

<400> SEQUENCE: 7

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser
        115

<210> SEQ ID NO 8
<211> LENGTH: 113
<212> TYPE: PRT
<213> ORGANISM: Artificial
<220> FEATURE:
<223> OTHER INFORMATION: anti-HER3 antibody (1) VL

<400> SEQUENCE: 8

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr

```
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys


<210> SEQ ID NO 9
<211> LENGTH: 447
<212> TYPE: PRT
<213> ORGANISM: Artificial Sequence
<220> FEATURE:
<223> OTHER INFORMATION: anti-HER3 antibody (1) H

<400> SEQUENCE: 9

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
            20                  25                  30

Tyr Trp Ser Trp Ile Arg Gln Pro Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Val Glu Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Trp Thr Trp Tyr Phe Asp Leu Trp Gly Arg Gly Thr Leu
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Leu Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445


<210> SEQ ID NO 10
<211> LENGTH: 220
<212> TYPE: PRT
<213> ORGANISM: Artificial Sequence
<220> FEATURE:
<223> OTHER INFORMATION: anti-HER3 antibody (1) L

<400> SEQUENCE: 10

Asp Ile Glu Met Thr Gln Ser Pro Asp Ser Leu Ala Val Ser Leu Gly
1               5                   10                  15

Glu Arg Ala Thr Ile Asn Cys Arg Ser Ser Gln Ser Val Leu Tyr Ser
            20                  25                  30

Ser Ser Asn Arg Asn Tyr Leu Ala Trp Tyr Gln Gln Asn Pro Gly Gln
        35                  40                  45

Pro Pro Lys Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys Gln Gln
                85                  90                  95

Tyr Tyr Ser Thr Pro Arg Thr Phe Gly Gln Gly Thr Lys Val Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220
```

METHOD FOR TREATING EGFR-TKI-RESISTANT NON-SMALL CELL LUNG CANCER BY ADMINISTRATION OF ANTI-HER3 ANTIBODY-DRUG CONJUGATE

CROSS-REFERENCE TO RELATED APPLICATIONS

The present application claims priority under 37 U.S.C. § 371 to International Patent Application No. PCT/JP2018/007152, filed Feb. 27, 2018, which claims priority to and the benefit of Japanese Patent Application Nos. 2017-035919, filed on Feb. 28, 2017, and 2017-199883, filed on Oct. 13, 2017. The contents of these applications are hereby incorporated by reference in their entireties.

TECHNICAL FIELD

The present invention relates to a therapeutic agent and a therapeutic method for EGFR-TKI-resistant non-small cell lung cancer, characterized by the administration of an anti-HER3 antibody-drug conjugate.

BACKGROUND ART

In the treatment with an EGFR tyrosine kinase inhibitor (EGFR-TKI) effective for epidermal growth factor receptor (EGFR) gene mutation-positive non-small cell lung cancer, drug resistance to the inhibitor is strengthened in many cases in the cancer to be treated as the treatment continues, and consequently, the disease progresses. Approximately half of the cancers resistant to gefitinib and erlotinib, which are first-generation EGFR-TKIs, and to afatinib, which is a second-generation EGFR-TKI, are known to have a T790M mutation in their EGFR genes. A third-generation EGFR-TKI, osimertinib, is known as a drug effective for non-small cell lung cancer in which the EGFR T790M mutation has been confirmed to be positive (cf. Non Patent Literature 1). However, no optimal drug for non-small cell lung cancer resistant to osimertinib has yet to be approved. In addition, no optimal drug for non-small cell lung cancer which has been confirmed to be resistant to EGFR-TKIs and negative for the EGFR T790M mutation has yet to be approved, either.

Human epidermal growth factor receptor 3 (HER3, also known as ErbB3) is a transmembrane receptor categorized in an epidermal growth factor receptor subfamily of receptor protein tyrosine kinases. An increase in the expression level of HER3 in cancer cells is known to be associated with the acquisition of resistance to EGFR-TKIs (cf. Non Patent Literature 2). Further, several studies have been conducted to test the effect of anti-HER3 antibodies on non-small cell lung cancer (cf. Non Patent Literature 3).

An antibody-drug conjugate (ADC) having a drug with cytotoxicity conjugated to an antibody, whose antigen is expressed on the surface of cancer cells and which also binds to an antigen capable of cellular internalization, and therefore can deliver the drug selectively to the cancer cells, is thus expected to cause accumulation of the drug within the cells and to kill the cancer cells (cf. Non Patent Literatures 4 to 8).

As one of the antibody-drug conjugates, an antibody-drug conjugate comprising an anti-HER3 antibody and exatecan, which is a topoisomerase I inhibitor, as components is known (cf. Patent Literature 1).

CITATION LIST

Patent Literature

Patent Literature 1: WO 2015/155998

Non Patent Literature

Non Patent Literature 1: I. Sullivan et al. Ther Adv Respir Dis 2016, Vol. 10(6) 549-565.

Non Patent Literature 2: N. V. Sergina et al. Nature 2007 January 25; 445(7126): 437-441.

Non Patent Literature 3: K Yonesaka et al., Oncogene (2016) 35, 878-886.

Non Patent Literature 4: Ducry, L., et al., Bioconjugate Chem. (2010) 21, 5-13.

Non Patent Literature 5: Alley, S. C., et al., Current Opinion in Chemical Biology (2010) 14, 529-537.

Non Patent Literature 6: Damle N. K. Expert Opin. Biol. Ther. (2004) 4, 1445-1452.

Non Patent Literature 7: Senter P. D., et al., Nature Biotechnology (2012) 30, 631-637.

Non Patent Literature 8: Howard A. et al., J Clin Oncol 29: 398-405.

SUMMARY OF INVENTION

Technical Problem

An object of the present invention is to provide a therapeutic agent and a therapeutic method for EGFR-TKI-resistant non-small cell lung cancer.

Solution to Problem

The inventors of the present invention have discovered that an anti-HER3 antibody-drug conjugate exhibits an excellent antitumor effect against EGFR-TKI-resistant non-small cell lung cancer.

That is, the present invention relates to the following:

[1] A therapeutic agent for EGFR-TKI-resistant non-small cell lung cancer, comprising an anti-HER3 antibody-drug conjugate as an active ingredient.

[2] The therapeutic agent according to [1], wherein the non-small cell lung cancer is EGFR T790M mutation-negative non-small cell lung cancer.

[3] The therapeutic agent according to [1] or [2], wherein the EGFR-TKI is gefitinib, erlotinib, afatinib, or osimertinib.

[4] The therapeutic agent according to [1] or [2], wherein the EGFR-TKI is osimertinib.

[5] The therapeutic agent according to [2], wherein the EGFR-TKI is gefitinib, erlotinib, or afatinib.

[6] The therapeutic agent according to [2], wherein the EGFR-TKI is gefitinib or erlotinib.

[7] The therapeutic agent according to any one of [1] to [6], wherein the non-small cell lung cancer expresses HER3.

[8] The therapeutic agent according to any one of [1] to [7], wherein the anti-HER3 antibody-drug conjugate is an anti-HER3 antibody-drug conjugate in which a drug-linker represented by the following formula:

[Formula 1]

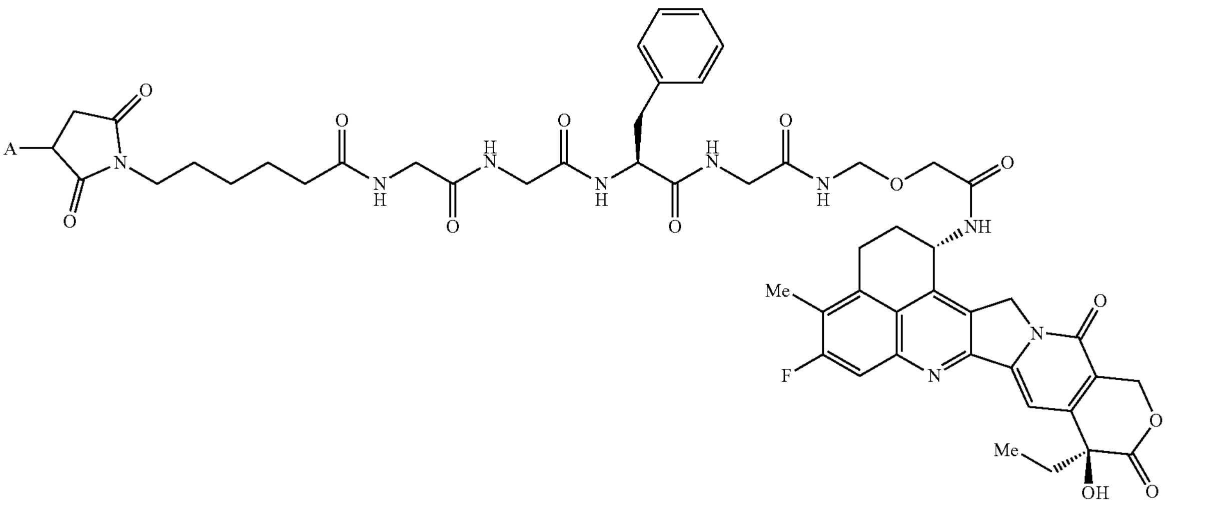

wherein A represents the connecting position to an anti-HER3 antibody, is conjugated to the anti-HER3 antibody via a thioether bond.

[9] The therapeutic agent according to any one of [1] to [8], wherein the anti-HER3 antibody is an antibody comprising a heavy chain comprising CDRH1 consisting of the amino acid sequence represented by SEQ ID NO:1, CDRH2 consisting of the amino acid sequence represented by SEQ ID NO:2, and CDRH3 consisting of the amino acid sequence represented by SEQ ID NO:3, and a light chain comprising CDRL1 consisting of the amino acid sequence represented by SEQ ID NO:4, CDRL2 consisting of the amino acid sequence represented by SEQ ID NO:5, and CDRL3 consisting of the amino acid sequence represented by SEQ ID NO:6.

[10] The therapeutic agent according to any one of [1] to [8], wherein the anti-HER3 antibody is an antibody comprising a heavy chain comprising a heavy chain variable region consisting of the amino acid sequence represented by SEQ ID NO:7, and a light chain comprising a light chain variable region consisting of the amino acid sequence represented by SEQ ID NO:8.

[11] The therapeutic agent according to any one of [1] to [8], wherein the anti-HER3 antibody is an antibody comprising a heavy chain consisting of the amino acid sequence represented by SEQ ID NO:9, and a light chain consisting of the amino acid sequence represented by SEQ ID NO:10.

[12] The therapeutic agent according to [11], wherein the anti-HER3 antibody lacks a lysine residue at the carboxyl terminus of the heavy chain.

[13] The therapeutic agent according to any one of [1] to [12], wherein the average number of units of the drug-linker conjugated per antibody molecule in the anti-HER3 antibody-drug conjugate is in the range of 7 to 8.

[14] The therapeutic agent according to any one of [1] to [12], wherein the average number of units of the drug-linker conjugated per antibody molecule in the anti-HER3 antibody-drug conjugate is in the range of 7.5 to 8.

[15] The therapeutic agent according to any one of [1] to [14], wherein the therapeutic agent is administered in combination with a second drug.

[16] The therapeutic agent according to [15], wherein the second drug is gefitinib, erlotinib, afatinib, or osimertinib.

[17] The therapeutic agent according to [16], wherein the second drug is erlotinib.

[18] The therapeutic agent according to [16], wherein the second drug is osimertinib.

[19] A therapeutic method for EGFR-TKI-resistant non-small cell lung cancer, comprising administering an anti-HER3 antibody-drug conjugate.

[20] The therapeutic method according to [19], wherein the non-small cell lung cancer is EGFR T790M mutation-negative non-small cell lung cancer.

[21] The therapeutic method according to [19] or [20], wherein the EGFR-TKI is gefitinib, erlotinib, afatinib, or osimertinib.

[22] The therapeutic method according to [19] or [20], wherein the EGFR-TKI is osimertinib.

[23] The therapeutic method according to [20], wherein the EGFR-TKI is gefitinib, erlotinib, or afatinib.

[24] The therapeutic method according to [20], wherein the EGFR-TKI is gefitinib or erlotinib.

[25] The therapeutic method according to any one of [19] to [24], wherein the non-small cell lung cancer expresses HER3.

[26] The therapeutic method according to any one of [19] to [25], wherein the anti-HER3 antibody-drug conjugate is an anti-HER3 antibody-drug conjugate in which a drug-linker represented by the following formula:

[Formula 2]

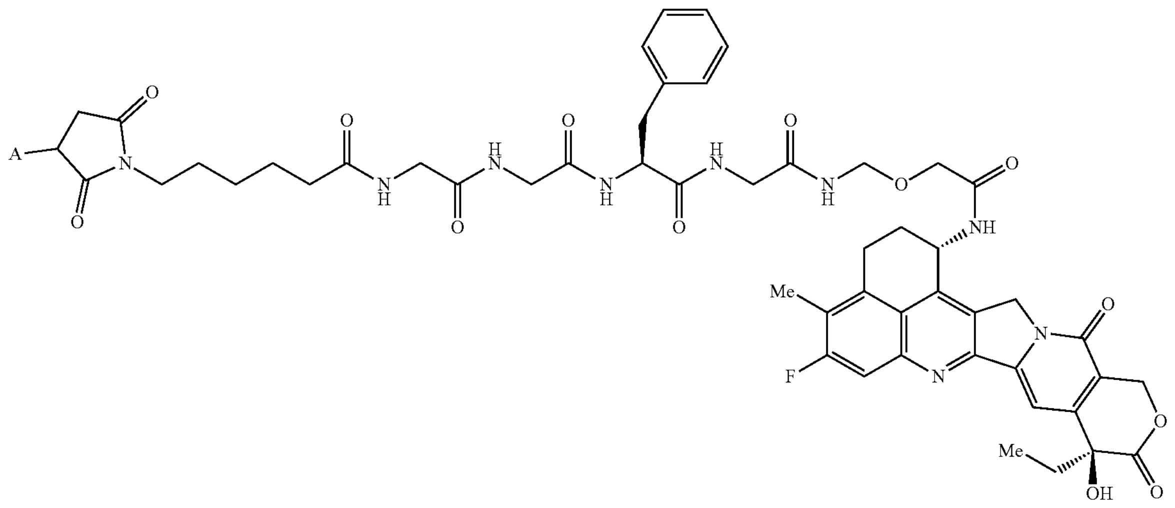

wherein A represents the connecting position to an anti-HER3 antibody, is conjugated to the anti-HER3 antibody via a thioether bond.

[27] The therapeutic method according to any one of [19] to [26], wherein the anti-HER3 antibody is an antibody comprising a heavy chain comprising CDRH1 consisting of the amino acid sequence represented by SEQ ID NO:1, CDRH2 consisting of the amino acid sequence represented by SEQ ID NO:2, and CDRH3 consisting of the amino acid sequence represented by SEQ ID NO:3, and a light chain comprising CDRL1 consisting of the amino acid sequence represented by SEQ ID NO:4, CDRL2 consisting of the amino acid sequence represented by SEQ ID NO:5, and CDRL3 consisting of the amino acid sequence represented by SEQ ID NO:6.

[28] The therapeutic method according to any one of [19] to [26], wherein the anti-HER3 antibody is an antibody comprising a heavy chain comprising a heavy chain variable region consisting of the amino acid sequence represented by SEQ ID NO:7, and a light chain comprising a light chain variable region consisting of the amino acid sequence represented by SEQ ID NO:8.

[29] The therapeutic method according to any one of [19] to [26], wherein the anti-HER3 antibody is an antibody comprising a heavy chain consisting of the amino acid sequence represented by SEQ ID NO:9, and a light chain consisting of the amino acid sequence represented by SEQ ID NO:10.

[30] The therapeutic method according to [29], wherein the anti-HER3 antibody lacks a lysine residue at the carboxyl terminus of the heavy chain.

[31] The therapeutic method according to any one of [19] to [30], wherein the average number of units of the drug-linker conjugated per antibody molecule in the anti-HER3 antibody-drug conjugate is in the range of 7 to 8.

[32] The therapeutic method according to any one of [19] to [30], wherein the average number of units of the drug-linker conjugated per antibody molecule in the anti-HER3 antibody-drug conjugate is in the range of 7.5 to 8.

[33] The therapeutic method according to any one of [19] to [32], wherein the anti-HER3 antibody-drug conjugate is administered in combination with a second drug.

[34] The therapeutic method according to [33], wherein the second drug is gefitinib, erlotinib, afatinib, or osimertinib.

[35] The therapeutic method according to [34], wherein the second drug is erlotinib.

[36] The therapeutic method according to [34], wherein the second drug is osimertinib.

[37] An anti-HER3 antibody-drug conjugate for the treatment of EGFR-TKI-resistant non-small cell lung cancer.

[38] The anti-HER3 antibody-drug conjugate according to [37], wherein the non-small cell lung cancer is EGFR T790M mutation-negative non-small cell lung cancer.

[39] The anti-HER3 antibody-drug conjugate according to [37] or [38], wherein the EGFR-TKI is gefitinib, erlotinib, afatinib, or osimertinib.

[40] The anti-HER3 antibody-drug conjugate according to [37] or [38], wherein the EGFR-TKI is osimertinib.

[41] The anti-HER3 antibody-drug conjugate according to [38], wherein the EGFR-TKI is gefitinib, erlotinib, or afatinib.

[42] The anti-HER3 antibody-drug conjugate according to [38], wherein the EGFR-TKI is gefitinib or erlotinib.

[43] The anti-HER3 antibody-drug conjugate according to any one of [37] to [42], wherein the non-small cell lung cancer expresses HER3.

[44] The anti-HER3 antibody-drug conjugate according to any one of [37] to [43], wherein the anti-HER3 antibody-drug conjugate is an anti-HER3 antibody-drug conjugate in which a drug-linker represented by the following formula:

[Formula 3]

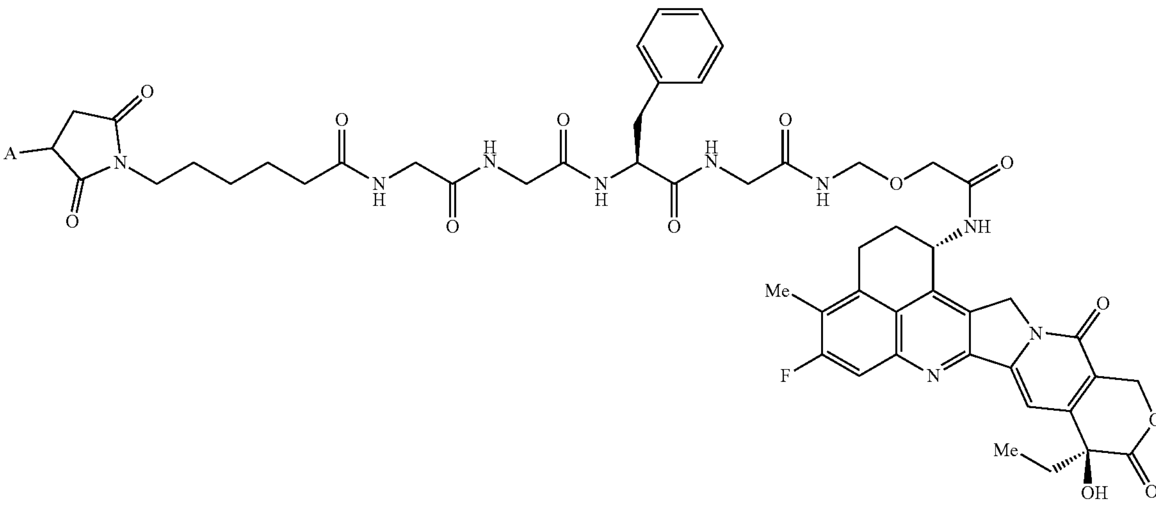

wherein A represents the connecting position to an anti-HER3 antibody, is conjugated to the anti-HER3 antibody via a thioether bond.

[45] The anti-HER3 antibody-drug conjugate according to any one of [37] to [44], wherein the anti-HER3 antibody is an antibody comprising a heavy chain comprising CDRH1 consisting of the amino acid sequence represented by SEQ ID NO:1, CDRH2 consisting of the amino acid sequence represented by SEQ ID NO:2, and CDRH3 consisting of the amino acid sequence represented by SEQ ID NO:3, and a light chain comprising CDRL1 consisting of the amino acid sequence represented by SEQ ID NO:4, CDRL2 consisting of the amino acid sequence represented by SEQ ID NO:5, and CDRL3 consisting of the amino acid sequence represented by SEQ ID NO:6.

[46] The anti-HER3 antibody-drug conjugate according to any one of [37] to [44], wherein the anti-HER3 antibody is an antibody comprising a heavy chain comprising a heavy chain variable region consisting of the amino acid sequence represented by SEQ ID NO:7, and a light chain comprising a light chain variable region consisting of the amino acid sequence represented by SEQ ID NO:8.

[47] The anti-HER3 antibody-drug conjugate according to any one of [37] to [44], wherein the anti-HER3 antibody is an antibody comprising a heavy chain consisting of the amino acid sequence represented by SEQ ID NO:9, and a light chain consisting of the amino acid sequence represented by SEQ ID NO:10.

[48] The anti-HER3 antibody-drug conjugate according to [47], wherein the anti-HER3 antibody lacks a lysine residue at the carboxyl terminus of the heavy chain.

[49] The anti-HER3 antibody-drug conjugate according to any one of [37] to [48], wherein the average number of units of the drug-linker conjugated per antibody molecule in the anti-HER3 antibody-drug conjugate is in the range of 7 to 8.

[50] The anti-HER3 antibody-drug conjugate according to any one of [37] to [48], wherein the average number of units of the drug-linker conjugated per antibody molecule in the anti-HER3 antibody-drug conjugate is in the range of 7.5 to 8.

[51] The anti-HER3 antibody-drug conjugate according to any one of [37] to [50], wherein the anti-HER3 antibody-drug conjugate is administered in combination with a second drug.

[52] The anti-HER3 antibody-drug conjugate according to [51], wherein the second drug is gefitinib, erlotinib, afatinib, or osimertinib.

[53] The anti-HER3 antibody-drug conjugate according to [52], wherein the second drug is erlotinib.

[54] The anti-HER3 antibody-drug conjugate according to [52], wherein the second drug is osimertinib.

[55] Use of an anti-HER3 antibody-drug conjugate for the manufacture of a medicament for the treatment of EGFR-TKI-resistant non-small cell lung cancer.

[56] The use according to [55], wherein the non-small cell lung cancer is EGFR T790M mutation-negative non-small cell lung cancer.

[57] The use according to [55] or [56], wherein the EGFR-TKI is gefitinib, erlotinib, afatinib, or osimertinib.

[58] The use according to [55] or [56], wherein the EGFR-TKI is osimertinib.

[59] The use according to [56], wherein the EGFR-TKI is gefitinib, erlotinib, or afatinib.

[60] The use according to [56], wherein the EGFR-TKI is gefitinib or erlotinib.

[61] The use according to any one of [55] to [60], wherein the non-small cell lung cancer expresses HER3.

[62] The use according to any one of [55] to [61], wherein the anti-HER3 antibody-drug conjugate is an anti-HER3 antibody-drug conjugate in which a drug-linker represented by the following formula:

[Formula 4]

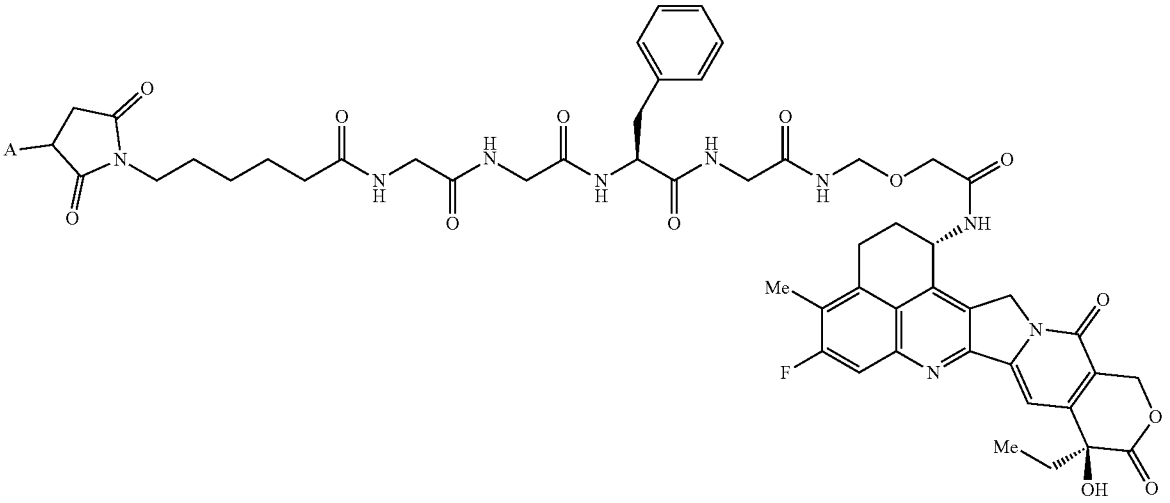

wherein A represents the connecting position to an anti-HER3 antibody, is conjugated to the anti-HER3 antibody via a thioether bond.

[63] The use according to any one of [55] to [62], wherein the anti-HER3 antibody is an antibody comprising a heavy chain comprising CDRH1 consisting of the amino acid sequence represented by SEQ ID NO:1, CDRH2 consisting of the amino acid sequence represented by SEQ ID NO:2, and CDRH3 consisting of the amino acid sequence represented by SEQ ID NO:3, and a light chain comprising CDRL1 consisting of the amino acid sequence represented by SEQ ID NO:4, CDRL2 consisting of the amino acid sequence represented by SEQ ID NO:5, and CDRL3 consisting of the amino acid sequence represented by SEQ ID NO:6.

[64] The use according to any one of [55] to [62], wherein the anti-HER3 antibody is an antibody comprising a heavy chain comprising a heavy chain variable region consisting of the amino acid sequence represented by SEQ ID NO:7, and a light chain comprising a light chain variable region consisting of the amino acid sequence represented by SEQ ID NO:8.

[65] The use according to any one of [55] to [62], wherein the anti-HER3 antibody is an antibody comprising a heavy chain consisting of the amino acid sequence represented by SEQ ID NO:9, and a light chain consisting of the amino acid sequence represented by SEQ ID NO:10.

[66] The use according to [65], wherein the anti-HER3 antibody lacks a lysine residue at the carboxyl terminus of the heavy chain.

[67] The use according to any one of [55] to [66], wherein the average number of units of the drug-linker conjugated per antibody molecule in the anti-HER3 antibody-drug conjugate is in the range of 7 to 8.

[68] The use according to any one of [55] to [66], wherein the average number of units of the drug-linker conjugated per antibody molecule in the anti-HER3 antibody-drug conjugate is in the range of 7.5 to 8.

[69] The use according to any one of [55] to [68], wherein the anti-HER3 antibody-drug conjugate is administered in combination with a second drug.

[70] The use according to [69], wherein the second drug is gefitinib, erlotinib, afatinib, or osimertinib.

[71] The use according to [70], wherein the second drug is erlotinib.

[72] The use according to [70], wherein the second drug is osimertinib.

Advantageous Effects of Invention

The present invention may provide a therapeutic agent and a therapeutic method for EGFR-TKI-resistant non-small cell lung cancer, characterized by the administration of an anti-HER3 antibody-drug conjugate.

BRIEF DESCRIPTION OF DRAWINGS

FIG. 1 shows the heavy chain amino acid sequence of anti-HER3 antibody (1).

FIG. 2 shows the light chain amino acid sequence of anti-HER3 antibody (1).

FIG. 3 is a graph showing the cell proliferation suppressing activity of HER3-ADC (1) on cell strain HCC827 and cell strain HCC827GR5. The error bars in the graph represent standard errors (n=6).

FIG. 4 is a graph showing HER3 mRNA levels in cell strain HCC827 and cell strain HCC827GR5.

FIG. 5 is a graph showing the cell proliferation suppressing activity of HER3-ADC (1) alone, erlotinib alone, or combined use of HER3-ADC (1) and erlotinib on cell strain HCC827GR5. The error bars in the graph represent standard errors (n=6).

FIG. 6 is a graph showing the antitumor effects of HER3-ADC (1) alone, erlotinib alone, or combined use of HER3-ADC (1) and erlotinib on cell strain HCC827GR5 transplanted in nude mice. The error bars in the graph represent standard deviations (n=10).

FIG. 7 is a graph showing the cell proliferation suppressing activity of osimertinib on cell strain PC9 and cell strain PC9AZDR7. The error bars in the graph represent standard errors (n=6).

FIG. 8 is a graph showing HER3 protein levels in cell strain PC9 and cell strain PC9AZDR7. The error bars in the graph represent standard deviations (n=3).

FIG. 9 is a graph showing the antitumor effects of HER3-ADC (1) alone on cell strain PC9 transplanted in nude mice. The error bars in the graph represent standard errors (control group: n=8, HER3-ADC (1) group: n=9), and the arrow represents administration of the drug.

FIG. 10 is a graph showing the antitumor effects of HER3-ADC (1) alone on cell strain PC9AZDR7 transplanted in nude mice. The error bars in the graph represent standard errors (control group: n=8, HER3-ADC (1) group: n=9), and the arrow represents administration of the drug.

FIG. 11 is a graph showing the antitumor effects of combined use of HER3-ADC (1) and osimertinib on cell strain PC9AZDR7 transplanted in nude mice. The error bars in the graph represent standard errors (control group: n=11, HER3-ADC (1) alone group: n=12, osimertinib alone group: n=12, combined use of HER3-ADC (1) and osimertinib group: n=10), and the arrows represent administration of each drug.

DESCRIPTION OF EMBODIMENTS

Hereinafter, preferable embodiments for carrying out the present invention will be described. Note that the embodiments described hereinafter merely show some examples of representative embodiments of the present invention, and the scope of the invention is not construed to be narrowed thereby.

In the present invention, the term "EGFR-TKI" represents an EGFR tyrosine kinase inhibitor, and may include, for example, gefitinib, erlotinib, afatinib, and osimertinib.

In the present invention, gefitinib and erlotinib may be referred to as the first-generation EGFR-TKI, afatinib may be referred to as the second-generation EGFR-TKI, and osimertinib may be referred to as the third-generation EGFR-TKI.

In the present invention, "EGFR-TKI-resistant non-small cell lung cancer" represents non-small cell lung cancer having been confirmed to exhibit resistance to one or more EGFR-TKIs, and non-small cell lung cancer which may reasonably be recognized or predicted to exhibit resistance to one or more EGFR-TKIs.

In the present invention, "EGFR T790M mutation" represents a mutation in which the $790^{th}$ amino acid, threonine, which is located in a gatekeeper region of the ATP binding site in the EGFR tyrosine kinase domain, has been converted to methionine (Pao W, et al., PLoS Med. 2(3):e73, 2005, Kobayashi S, et al., N Engl J Med. 352(8):786-792, 2005). The presence or absence of the EGFR T790M mutation may be determined by collecting a tissue specimen or a blood plasma specimen from a patient with non-small cell lung cancer, and subjecting the specimen to real-time PCR or other methods.

In the present invention, "EGFR T790M mutation positive non-small cell lung cancer" represents non-small cell lung cancer which has been confirmed to be positive for the EGFR T790M mutation, and non-small cell lung cancer which may reasonably be recognized or predicted to be positive for the EGFR T790M mutation.

EGFR T790M mutation-positive non-small cell lung cancer is considered to have an altered steric structure of the ATP binding site in EGFR and thereby exhibits resistance to first-generation EGFR-TKIs and second-generation EGFR-TKIs through a mechanism such as steric hindrance, and this has been observed in approximately half of the cases where the cancer exhibits resistance to first-generation EGFR-TKIs and second-generation EGFR-TKIs. A third-generation EGFR-TKI, osimertinib, is known as a drug effective for EGFR T790M mutation-positive non-small cell lung cancer.

No optimal drug for osimertinib-resistant non-small cell lung cancer has been approved yet, and there is an unmet medical need.

Examples of cell strains corresponding to osimertinib-resistant non-small cell lung cancer may include cell strain PC9AZDR7. Cell strain PC9AZDR7 is a cell strain derived from PC9, a human non-small cell lung cancer cell strain, and has acquired resistance to osimertinib. This cell strain may be established by the method described in Example 3-1 of the present description.

The antitumor effect of a drug on osimertinib-resistant non-small cell lung cancer may be determined by testing the drug for its in vitro cell proliferation suppressing activity on the above-mentioned cell strain, or its in vivo tumor proliferation suppression ratio in a model in which the above-mentioned cell line is transplanted into nude mice.

In the present invention, "EGFR T790M mutation-negative non-small cell lung cancer" represents non-small cell lung cancer having been confirmed to be negative for the EGFR T790M mutation, and non-small cell lung cancer which may reasonably be recognized or predicted to be negative for the EGFR T790M mutation.

Among the EGFR-TKI-resistant cases, the cases other than EGFR T790M mutation-positive non-small cell lung cancer correspond to EGFR T790M mutation-negative non-small cell lung cancer. Such EGFR T790M mutation-negative non-small cell lung cancer is considered to have acquired the resistance by a mutation other than the EGFR T790M mutation (for example, amplification of MET gene) or the like; however, the existence of unknown resistance mechanisms has also been suggested.

No optimal drug for EGFR T790M mutation-negative non-small cell lung cancer exhibiting resistance to EGFR-TKIs has been approved yet, and there is an unmet medical need.

Examples of cell strains corresponding to EGFR T790M mutation-negative non-small cell lung cancer exhibiting resistance to EGFR-TKIs may include cell strain HCC827GR5 (Engelman J A et al., Science 2007, 316 (5827), 1039-1043). Cell strain HCC827GR5 is a cell strain derived from HCC827, a human non-small cell lung cancer cell strain and has acquired resistance to gefitinib, which is an EGFR-TKI. Further, cell strain 11-18 (Proc Natl Acad Sci USA, Jul. 31, 2012; 109 (31): E2127-33) or cell strain Ma70GR (K. Yonesaka et al., Oncogene (2016) 35, 878-886) may also be used as a cell strain corresponding to EGFR T790M mutation-negative non-small cell lung cancer exhibiting resistance to EGFR-TKIs.

The antitumor effect of a drug on EGFR T790M mutation-negative non-small cell lung cancer exhibiting resistance to EGFR-TKIs may be determined by testing the drug for its in vitro cell proliferation suppressing activity on the above-mentioned cell strains, or its in vivo tumor proliferation suppression ratio in a model in which the above-mentioned cell strains are transplanted into nude mice.

In the present invention, "HER3" has the same meaning as human epidermal growth factor receptor 3 (also referred to as ErbB3) and is a transmembrane receptor categorized in an epidermal growth factor receptor subfamily of receptor protein tyrosine kinase together with HER1, HER2, and HER4. HER3 is expressed in many kinds of cancer cells such as breast cancer, gastrointestinal cancer, pancreatic cancer, etc. and is known to form a heterodimer with a tyrosine kinase receptor such as EGFR or HER2 whereby HER3 itself is phosphorylated and then induces cancer proliferation or apoptosis inhibitory signals.

HER3 proteins used for the present invention may be used directly after being purified from human HER3-expressing cells or, when used as antigens, a cellular membrane fraction of the cells may be used as HER3 proteins. Furthermore, HER3 proteins may be obtained by synthesizing HER3 in vitro, or rendering host cells produce HER3 by genetic manipulation. Specifically, in the genetic manipulation, HER3 may be synthesized by incorporating HER3 cDNA into a vector capable of expressing HER3 cDNA, and then incubating the vector in a solution comprising enzymes, substrates, and energy sources required for the transcription and translation. Alternatively, the proteins may be obtained by transforming other prokaryote or eukaryote host cells with the vector to express HER3. Furthermore, the HER3-expressing cells obtained by the genetic manipulation described above or a cell strain expressing HER3 may be also used as HER3 protein antigens.

The RNA sequence, cDNA sequence, and amino acid sequence of HER3 have been disclosed on several official public databases. For example, they may be referenced with accession numbers such as AAA35979 (a precursor comprising a signal sequence consisting of the amino-terminal 19 amino acid residues), M34309 (NCBI), etc.

Furthermore, HER3 includes a protein consisting of an amino acid sequence where 1 to 10 amino acid substitution, deletion, addition, and/or insertion has been made to the amino acid sequence of HER3, but keeping a biological activity equivalent to the protein.

In the present invention, the term "anti-HER3 antibody" represents an antibody that specifically binds to HER3, and preferably has an activity of being internalized into HER3-expressing cells by binding to HER3, in other words, has an activity of binding to HER3 and then migrating into HER3-expressing cells.

Anti-HER3 antibodies used in the present invention may be obtained by known means. For example, by means of methods conventionally carried out in this field, the antibodies may be obtained by immunizing an animal with, as an antigen, HER3 or any polypeptide selected from the amino acid sequence of HER3, and then collecting and purifying antibodies produced in vivo. The origin of the antigen is not limited to humans, and an antigen derived from non-human animals such as mice or rats may be used to immunize an animal. In this case, anti-HER3 antibodies applicable to human diseases may be screened by testing the obtained antibodies that bind to the heterologous antigen for their cross-reactivity with the human antigen.

Alternatively, according to the known methods (for example, Kohler and Milstein, Nature (1975) 256, pp. 495-497; Kennet, R. ed., Monoclonal Antibodies, pp. 365-367, Plenum Press, N.Y. (1980), monoclonal antibodies may be obtained by fusing antibody-producing cells producing an antibody against the antigen with myeloma cells to establish a hybridoma.

Meanwhile, the antigen may be obtained by rendering host cells produce a gene encoding the antigen protein by genetic manipulation. Specifically, it may be attained by preparing a vector capable of expressing the antigen gene, introducing the vector into a host cell to express the gene, and purifying the antigen thus expressed. The antibodies may also be obtained by immunizing an animal with the antigen-expressing cells obtained by the aforementioned genetic manipulation or a cell strain expressing the antigen.

The anti-HER3 antibody used in the present invention is preferably a gene recombinant antibody such as a chimeric antibody or a humanized antibody, which has been artificially modified for the purpose of reducing the heterologous antigenicity to humans, or an antibody having only the gene sequence of a human-derived antibody, that is, a human antibody. These antibodies may be produced using known methods.

Examples of the chimeric antibody may include an antibody in which the variable and constant regions of the antibody are heterologous to each other, for example, a chimeric antibody in which the variable region of a mouse- or rat-derived antibody is conjugated to the constant region derived from humans (Proc. Natl. Acad. Sci. U.S.A., 81, pp. 6851-6855 (1984)).

Examples of the humanized antibody may include an antibody in which only the complementarity determining region (CDR) of a heterologous antibody is incorporated into a human-derived antibody (Nature (1986) 321, pp. 522-525), an antibody in which not only the CDR sequence of a heterologous antibody but also some framework amino acid residues of the heterologous antibody are grated into a human antibody by CDR grafting (WO 90/07861), and an antibody that has been humanized using gene conversion mutagenesis strategies (U.S. Pat. No. 5,821,337).

Examples of the human antibody may include an antibody prepared using a human antibody-producing mouse having a human chromosome fragment comprising heavy and light chain genes of a human antibody (see Tomizuka, K. et al., Nature Genetics (1997) 16, pp. 133-143; Kuroiwa, Y. et al., Nucl. Acids Res. (1998) 26, pp. 3447-3448; Yoshida, H. et al., Animal Cell Technology: Basic and Applied Aspects Vol. 10, pp. 69-73 (Kitagawa, Y., Matsuda, T. and Iijima, S. eds.), Kluwer Academic Publishers, 1999; Tomizuka, K. et al., Proc. Natl. Acad. Sci. USA (2000) 97, pp. 722-727; and the like). Alternatively, examples of the human antibody may include an antibody screened from human antibody libraries by phage display (see Wormstone, I. M. et al., Investigative Ophthalmology & Visual Science, (2002)43(7), pp. 2301-2308; Carmen, S. et al., Briefings in Functional Genomics and Proteomics (2002), 1(2), pp. 189-203; Siriwardena, D. et al., Ophthalmology (2002) 109(3), pp. 427-431; and the like).

The anti-HER3 antibody used in the present invention also includes modified forms of antibodies. The modified form means a compound in which some chemical or biological modification has been made to the antibody of the present invention. Examples of the chemically modified forms may include chemically modified forms in which some chemical moiety is bound to an amino acid backbone, or in which some chemical moiety is bound to an N-linked or O-linked hydrocarbon chain. Examples of biologically modified forms may include a compound to which a post-translational modification (for example, addition of N-linked or O-linked sugar chains, N- or C-terminal processing, deamidation, isomerization of aspartic acid, and oxidation of methionine) has been added, and a compound having a methionine residue added to its N-terminus by using a prokaryotic host cell to express the compound. Furthermore, the modified forms may include compounds that have been labeled in order to enable detection or isolation of the anti-HER3 antibody or the antigen used in the present invention, for example, compounds labeled with enzymatic or fluorescent markers, or compounds labeled for affinity. Such modified forms of the anti-HER3 antibody used in the present invention are useful for the improvement of stability and blood retentivity of the antibody, reduction of antigenicity, detection or isolation of the antibody or antigen, and the like.

Furthermore, modulating the sugar chain modification (glycosylation, defucosylation, or the like) linked to the anti-HER3 antibody used in the present invention may lead to enhancement of the antibody-dependent cellular cytotoxicity activity. Regarding the technology for modulating the sugar chain modification of antibodies, WO 99/54342, WO 00/61739, WO 02/31140, and the like are known; however, the technologies are not limited to these. The anti-HER3 antibody used in the present invention includes antibodies in which one or more sugar chain modifications have been modulated.

It is known that a lysine residue at the carboxyl terminus of the heavy chain is deleted in antibodies produced in cultured mammalian cells (Journal of Chromatography A, 705: 129-134 (1995)). It is also known that two amino acid residues, glycine and lysine, at the carboxyl terminus of the heavy chain are deleted, and the proline residue newly located at the carboxyl terminus is amidated (Analytical Biochemistry, 360: 75-83 (2007)). However, these deletions and modifications in heavy chain sequences do not affect the antigen-binding ability and effector function (such as complement activation and antibody-dependent cellular cytotoxicity) of the antibodies. Therefore, the anti-HER3 antibody used in the present invention also includes an antibody having received the modification and a functional fragment thereof, and a deletant in which one or two amino acids have been deleted at the heavy chain carboxyl terminus and a deletant that has been also amidated (for example, a heavy chain in which the proline residue at the carboxyl terminal site has been amidated). However, as long as the antigen binding ability and effector function are maintained, the deletant having a deleted heavy chain carboxyl terminus of the anti-HER3 antibody used in the present invention is not limited to those mentioned above. The two heavy chains constituting the anti-HER3 antibody used in the present invention may be derived from a single kind of heavy chain selected from the group consisting of the full length and the above-described deletants, or may be a combination of any two kinds. The quantitative ratio of each deletant may be affected by the cultured mammalian cells that produce the anti-HER3 antibody used in the present invention, and the culture conditions; however, the anti-HER3 antibody used in the present invention is preferably an anti-HER3 antibody having two heavy chains, each of which has one amino acid residue deletion at its carboxyl terminus.

Examples of isotypes of the anti-HER3 antibody used in the present invention may include IgG (IgG1, IgG2, IgG3, and IgG4), and a preferred isotype may be IgG1 or IgG2. Furthermore, modification forms of these may also be used as the anti-HER3 antibody in the present invention.

Examples of the anti-HER3 antibody used in the present invention include patritumab (U3-1287), U1-59 (WO 2007/077028), AV-203 (WO 2011/136911), LJM-716 (WO 2012/022814), duligotumab (MEHD-7945A) (WO 2010/108127), istiratumab (MM-141) (WO 2011/047180), lumretuzumab (RG-7116) (WO 2014/108484), setibantumab (MM-121) (WO 2008/100624), REGN-1400 (WO 2013/048883), ZW-9 (WO 2013/063702), and modified forms, active fragments, and modification forms thereof. Preferable examples of the antibody include patritumab and U1-59. These anti-HER3 antibodies may be produced by the methods described in the literatures mentioned above.

In the present invention, the term "antibody-drug conjugate" represents a complex in which an antibody is conjugated to a drug having cytotoxicity through a linker. Examples of the antibody-drug conjugate include those described in U.S. Pat. No. 6,214,345, WO 2002/083067, WO 2003/026577, WO 2004/054622, WO 2005/112919, WO 2006/135371, WO 2007/112193, WO 2008/033891, WO 2009/100194, WO 2009/134976, WO 2009/134977, WO 2010/093395, WO 2011/130613, WO 2011/130616, WO 2013/055993, WO 2014/057687, WO 2014/061277, WO 2014/107024, WO 2014/134457, and WO 2014/145090. Preferable examples of the conjugate include the antibody-drug conjugates described in WO 2014/057687 and WO 2014/061277, and more preferable examples include the conjugates described in WO 2014/057687. These antibody-drug conjugates may be produced by the methods described in the above-mentioned literatures.

The drug having cytotoxicity is not particularly limited as long as it has an antitumor effect and has a substituent or a partial structure capable of binding to a linker. Examples of the drug include camptothecin, calicheamicin, doxorubicin, daunorubicin, mitomycin C, bleomycin, cyclocytidine, vincristine, vinblastine, methotrexate, cisplatin, auristatin E, maytansine, paclitaxel, pyrrolobenzodiazepine, and derivatives thereof. Preferable examples include camptothecin derivatives, and more preferable examples include exatecan derivatives. Exatecan (IUPAC name: (1S,9S)-1-amino-9-ethyl-5-fluoro-1,2,3,9,12,15-hexahydro-9-hydroxy-4-methyl-10H,13H-benzo[de]pyrano[3',4':6,7]indolidino[1,2-b]quinoline-10,13-dione, also indicated as chemical name: ((1S,9S)-1-amino-9-ethyl-5-fluoro-2,3-dihydro-9-hydroxy-4-methyl-1H,12H-benzo[de]pyrano[3',4':6,7]indolidino[1,2-b]quinoline-10,13(9H,15H)-dione), which is a topoisomerase I inhibitor, is a compound represented by the following formula:

[Formula 5]

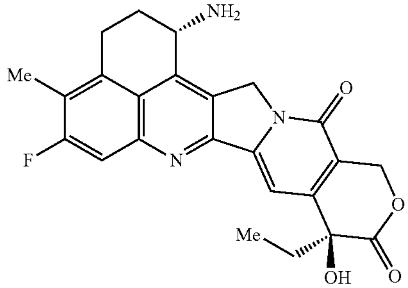

In the present invention, the "drug-linker" represents a drug and linker moiety in an antibody-drug conjugate, in other words, a partial structure other than the antibody moiety in an antibody-drug conjugate.

In the present invention, the "anti-HER3 antibody-drug conjugate" represents an antibody-drug conjugate in which the antibody in the antibody-drug conjugate is an anti-HER3 antibody. Examples of the anti-HER3 antibody-drug conjugate include those described in WO 2012/019024, WO 2012/064733, and WO 2015/155998, and preferable examples thereof include those described in WO 2015/155998. These anti-HER3 antibody-drug conjugates may be produced by the methods described in the above-mentioned literatures.

The anti-HER3 antibody-drug conjugate more preferably used in the present invention is an anti-HER3 antibody-drug conjugate in which a drug-linker represented by the following formula:

[Formula 6]

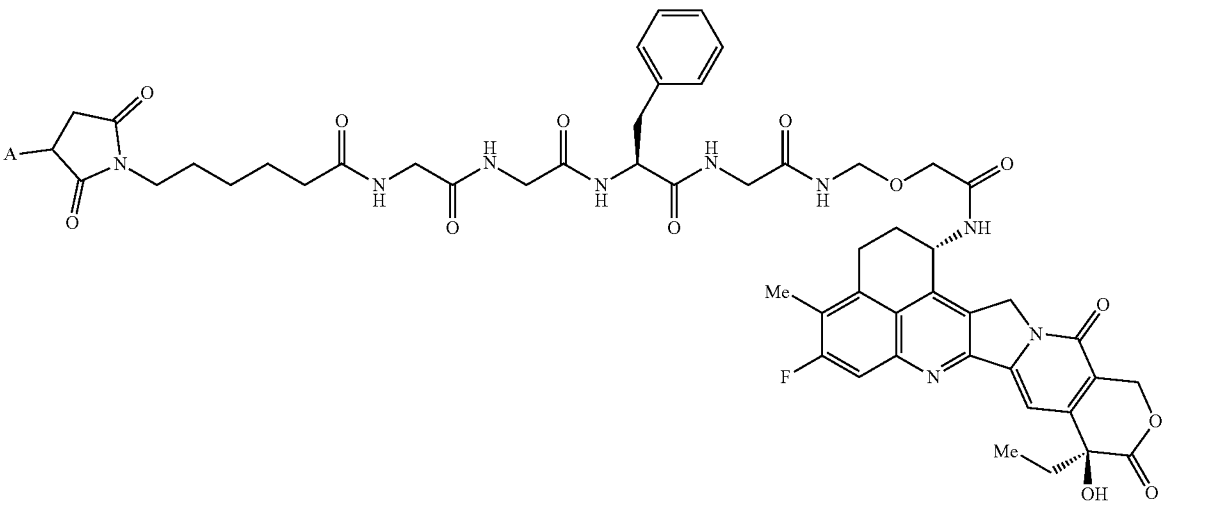

wherein A represents the connecting position to an anti-HER3 antibody, is conjugated to the anti-HER3 antibody via a thioether bond. This drug-linker is connected to a thiol group (in other words, a sulfur atom of a cysteine residue) formed at one or more interchain disulfide bond sites of the antibody (two sites between heavy chains, and two sites between a heavy chain and a light chain).

The anti-HER3 antibody-drug conjugate more preferably used in the present invention may also be represented by the following formula:

[Formula 7]

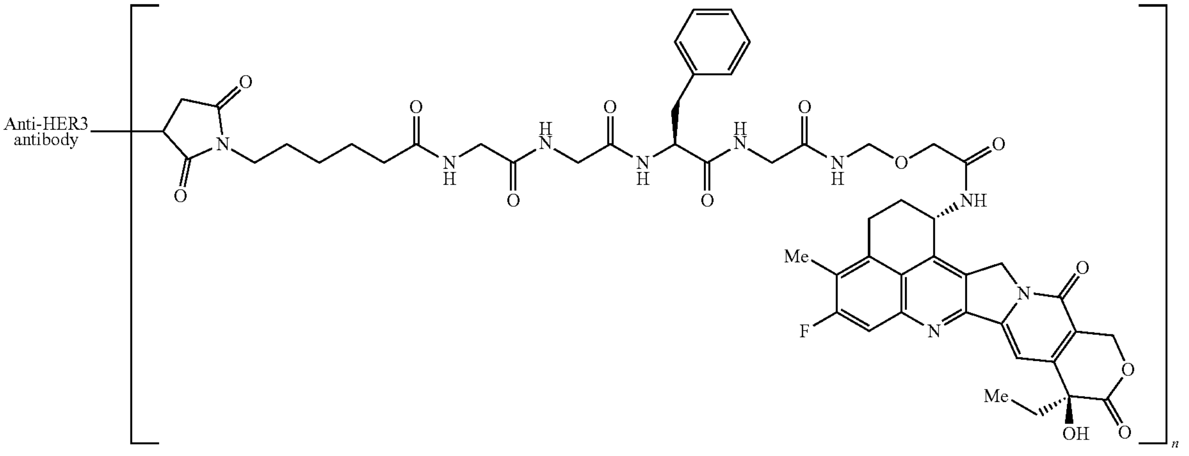

In the above formula, the drug-linker is conjugated to the antibody by a thioether bond. The meaning of n is the same as that of what is called the average number of conjugated drug molecules (DAR; Drug-to-Antibody Ratio), and indicates the average number of units of the drug-linker conjugated per antibody molecule.

An anti-HER3 antibody-drug conjugate more preferably used in the present invention undergoes cleavage of the linker part after being transferred into a tumor cell and then release a compound represented by the following formula:

[Formula 8]

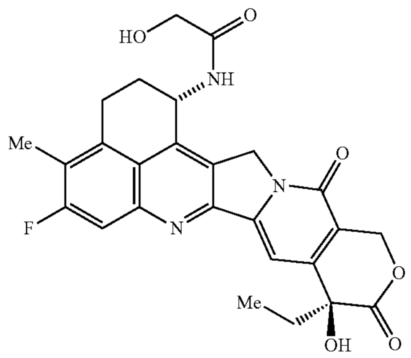

The compound is considered to be a main body imparting the antitumor activity of the anti-HER3 antibody-drug conjugate more preferably used in the present invention, and has been confirmed to have a topoisomerase I inhibitory activity (Ogitani Y. et al., Clinical Cancer Research, 2016, Oct. 15; 22(20):5097-5108, Epub 2016 Mar. 29).

The anti-HER3 antibody moiety in the anti-HER3 antibody-drug conjugate used in the present invention is preferably an antibody comprising a heavy chain comprising CDRH1 consisting of the amino acid sequence represented by SEQ ID NO:1, CDRH2 consisting of the amino acid sequence represented by SEQ ID NO:2, and CDRH3 consisting of the amino acid sequence represented by SEQ ID NO:3; and a light chain comprising CDRL1 consisting of the amino acid sequence represented by SEQ ID NO:4, CDRL2 consisting of the amino acid sequence represented by SEQ ID NO:5, and CDRL3 consisting of the amino acid sequence represented by SEQ ID NO:6, more preferably an antibody comprising a heavy chain comprising a heavy chain variable region consisting of the amino acid sequence represented by SEQ ID NO:7; and a light chain comprising a light chain variable region consisting of the amino acid sequence represented by SEQ ID NO:8, and even more preferably, an antibody comprising a heavy chain consisting of the amino acid sequence represented by SEQ ID NO:9; and a light chain consisting of the amino acid sequence represented by SEQ ID NO:10, or an antibody comprising the same sequences as those mentioned above except that the antibody lacks a lysine residue at the carboxyl terminus of one or both heavy chains.

A drug-linker intermediate used in the production of the anti-HER3 antibody-drug conjugate may be represented by the following formula:

[Formula 9]

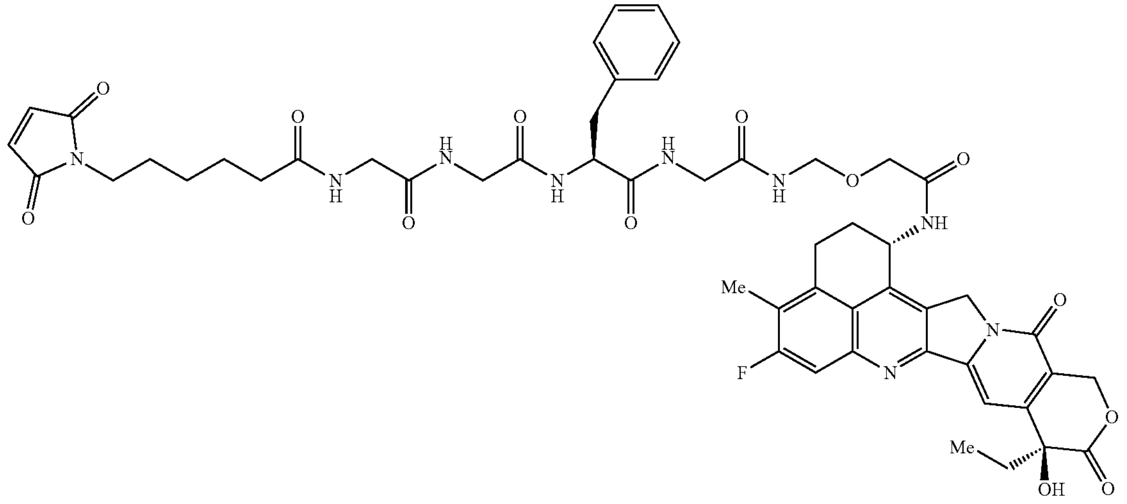

The drug-linker intermediate may be represented by a chemical name: N-[6-(2,5-dioxo-2,5-dihydro-1H-pyrrol-1-yl)hexanoyl]glycylglycyl-L-phenylalanyl-N-[(2-{[(1S,9S)-9-ethyl-5-fluoro-9-hydroxy-4-methyl-10,13-dioxo-2,3,9,10,13,15-hexahydro-1H,12H-benzo[de]pyrano[3',4':6,7]indolidino[1,2-b]quinolin-1-yl]amino}-2-oxoethoxy)methyl]glycinamide. The drug-linker intermediate may be produced by referring to the disclosures in WO 2014/057687, WO 2015/155998, and the like.

An anti-HER3 antibody-drug conjugate preferably used in the present invention may be produced by reacting the above-mentioned drug-linker intermediate with an anti-HER3 antibody having a thiol group (or also referred to as a sulfhydryl group).

The anti-HER3 antibody having a sulfhydryl group may be obtained by methods well known to those having ordinary skill in the art (e.g., Hermanson, G. T., Bioconjugate Techniques, pp. 56-136, pp. 456-493, Academic Press (1996)). For example, the anti-HER3 antibody having a sulfhydryl group in which interchain disulfides are partially or completely reduced may be obtained by reacting an anti-HER3 antibody with a reducing agent such as tris(2-carboxyethyl)phosphine hydrochloride (TCEP) in an amount of 0.3 to 3 molar equivalents with respect to one interchain disulfide in a buffer solution including a chelating agent such as ethylenediaminetetraacetic acid (EDTA).

Further, by using 2 to 20 molar equivalents of the drug-linker intermediate per the anti-HER3 antibody having a sulfhydryl group, an anti-HER3 antibody-drug conjugate in which 2 to 8 drug molecules are conjugated per antibody molecule can be produced.

The average number of conjugated drug molecules per antibody molecule in the anti-HER3 antibody-drug conjugate produced may be determined by, for example, a method of calculation based on measurement of UV absorbance for the anti-HER3 antibody-drug conjugate and the conjugation precursor thereof at two wavelengths of 280 nm and 370 nm (UV method), or a method of calculation based on quantification through HPLC measurement for fragments obtained by treating the antibody-drug conjugate with a reducing agent (HPLC method).

Conjugation between the anti-HER3 antibody and the drug-linker intermediate and calculation of the average number of conjugated drug molecules per antibody molecule in the anti-HER3 antibody-drug conjugate may be performed by referring to the disclosures in WO 2015/155998 and the like.

The average number of units of the drug-linker conjugated per antibody molecule in the anti-HER3 antibody-drug conjugate used in the present invention is preferably from 2 to 8, more preferably from 3 to 8, even more preferably from 7 to 8, still more preferably from 7.5 to 8, and even further preferably about 8.

A therapeutic agent and a therapeutic method of the present invention have a feature of administering an anti-HER3 antibody-drug conjugate, and may be used for the treatment of EGFR-TKI-resistant non-small cell lung cancer. The "non-small cell lung cancer" may be EGFR T790M mutation-negative non-small cell lung cancer, or EGFR T790M mutation-positive non-small cell lung cancer.

The "EGFR-TKI" in the "EGFR-TKI-resistant non-small cell lung cancer" is preferably gefitinib, erlotinib, afatinib, or osimertinib, and more preferably osimertinib. Further, when the "non-small cell lung cancer" in the "EGFR-TKI-resistant non-small cell lung cancer" is EGFR T790M mutation-negative non-small cell lung cancer, the "EGFR-TKI" is preferably gefitinib, erlotinib, or afatinib, and more preferably gefitinib or erlotinib.

The "EGFR-TKI-resistant non-small cell lung cancer" preferably expresses HER3, and more preferably expresses a high level of HER3. Expression of HER3 may be checked by, for example, detection of HER3 gene products (proteins) by means of immunohistochemistry (IHC), flow cytometer, Western blotting, or the like, or detection of HER3 gene transcription by means of in situ hybridization (ISH) or quantitative PCR (q-PCR). Whether HER3 is highly expressed or not may be determined by using any methods well known to those having ordinary skill in the art.

The therapeutic agent and the therapeutic method of the present invention may include one or more additional drugs (for example, a second drug) in addition to the anti-HER3 antibody-drug conjugate used in the present invention. That is, the therapeutic agent or the anti-HER3 antibody-drug conjugate used in the present invention may be administered in combination with one or more additional drugs, and thereby an anticancer effect may be augmented. The additional drug used for this purpose may be administered to an individual simultaneously, separately, or sequentially with the anti-HER3 antibody-drug conjugate used in the present invention, or may be administered with changing the interval of administration of each. The additional drug or the second drug is preferably a therapeutic agent for cancer. The therapeutic agent for cancer is not particularly limited as long as it has an antitumor activity. The therapeutic agent for cancer is, for example, at least one selected from the group consisting of EGFR-TKIs, cisplatin, carboplatin, oxaliplatin, paclitaxel, docetaxel, gemcitabine, capecitabine, irinotecan (CPT-11), etoposide, cyclophosphamide, doxorubicin, vinblastin, and vincristine, and the therapeutic agent for cancer is more preferably EGFR-TKIs.

The EGFR-TKI mentioned above is preferably gefitinib, erlotinib, afatinib, or osimertinib; more preferably erlotinib or osimertinib; and even more preferably osimertinib.

The therapeutic agent and therapeutic method of the present invention may be chosen and used as a drug for pharmacotherapy, which is a major therapy for cancer treatment. As a result, the therapeutic agent and therapeutic method of the present invention may retard the growth of cancer cells, suppress their proliferation, and destroy cancer cells. Through these actions, relief from cancer-induced symptoms and improved QOL may be achieved in cancer patients, the lives of the cancer patients are maintained, and thereby the therapeutic effects can be achieved. Even if cancer cells are not destroyed, longer survival and higher QOL can be achieved in cancer patients through suppression or control of the proliferation of cancer cells.

In addition to the use of the drug alone in such pharmacotherapy, the therapeutic agent and therapeutic method of the present invention may also be used in adjuvant therapies as a drug to be combined with another therapy. It may be combined with surgical operations, radiation therapy, hormone therapy, and the like. Furthermore, the therapeutic agent and therapeutic method may also be used as a drug for pharmacotherapy in neoadjuvant therapies.

In addition to the therapeutic uses as stated above, the therapeutic agent and therapeutic method of the present invention is expected to provide a prophylactic effect for inhibiting the proliferation of minute metastatic cancer cells and/or destroying them. For example, it is expected to provide an effect on suppressing and/or destroying cancer cells in the body fluid during the process of metastasis, or on suppressing and/or destroying minute cancer cells immediately after implantation into any tissues. Therefore, in particular, an effect of suppressing and preventing cancer metastasis after surgical removal of cancer may be expected.

The therapeutic agent and therapeutic method of the present invention may be applied not only as system therapy but also locally to cancer tissues in a patient, and thereby a therapeutic effect may be expected.

The therapeutic agent and therapeutic method of the present invention may be preferably used for mammals, and more preferably for humans.

The therapeutic agent of the present invention may be administered as a pharmaceutical composition comprising one or more pharmaceutically acceptable ingredients. The substances to be used for the pharmaceutical composition of the present invention may be appropriately selected from the formulation additives or others conventionally used in this field in appropriate amounts or concentrations of administration. For example, the pharmaceutical composition representatively comprises one or more pharmaceutical carriers (for example, a sterilized liquid). Examples of the liquid include water and oil (petroleum, oil from animal origins, oil from plant origins, or oil from synthetic origins). The oil may be, for example, peanut oil, soybean oil, mineral oil, or sesame oil. Water is a more representative carrier when the pharmaceutical composition is intravenously administered. A saline solution, an aqueous dextrose solution, and an aqueous glycerol solution may also be used as liquid carriers and particularly as injectable solutions. Appropriate pharmaceutical excipients may be selected as appropriate from those well known in this field. The pharmaceutical composition may comprise, if desired, a trace amount of a wetting agent, an emulsifier, or a pH buffering agent. Appropriate examples of the pharmaceutical carrier are described in "Remington's Pharmaceutical Sciences" written by E. W. Martin. The prescription thereof corresponds to the mode of administration.

Various delivery systems are known and may be used to administer the pharmaceutical composition of the present invention. Examples of the route of introduction include intradermal, intramuscular, intraperitoneal, intravenous, and subcutaneous routes; however, the route of administration is not intended to be limited to these. The administration may be made by, for example, infusion or bolus injection. In a particular preferred embodiment, the administration of the antibody-drug conjugate is made by infusion. Parenteral administration is a preferred route of administration.

In a representative embodiment, the pharmaceutical composition is formulated as a composition suitable for intravenous administration into humans according to the routine procedures. Representatively, the composition for intravenous administration is a solution in a sterilized, isotonic aqueous buffer. If necessary, the pharmaceutical composition may comprise a solubilizing agent and a local anesthetic agent (for example, lignocaine) for alleviating pain at the site of injection. Generally, these ingredients are supplied, for example, either separately as a dried freeze-dried powder or anhydrous concentrate in a sealed container such as an ampoule, a sachet, or the like, which indicates the amount of the active agent, or altogether as a mixture in a unit dosage. In embodiments where the pharmaceutical composition is administered by infusion, it may be administered, for example, with an infusion bottle containing pharmaceutical grade sterile water or saline. In embodiments where the medicine is administered by injection, the ampoule containing sterile water or saline for injection may be provided so that the above-described ingredients can be mixed to each other before administration.

The amount of administration per dose of the anti-HER3 antibody-drug conjugate used in the present invention is preferably in the range of 1.6 mg/kg to 12.4 mg/kg; more preferably 3.2 mg/kg, 4.8 mg/kg, 6.4 mg/kg, 8 mg/kg, 9.6 mg/kg, or 12.4 mg/kg; and even more preferably 4.8 mg/kg, 6.4 mg/kg, 8 mg/kg, 9.6 mg/kg, or 12.4 mg/kg.

In embodiments where the anti-HER3 antibody-drug conjugate used in the present invention is used in combination with a second drug (preferably an EGFR-TKI, more preferably erlotinib or osimertinib, and even more preferably osimertinib), the amount of administration per dose of the anti-HER3 antibody-drug conjugate used in the present invention is preferably in the range of 0.8 mg/kg to 12.4 mg/kg; more preferably 1.6 mg/kg, 3.2 mg/kg, 4.8 mg/kg, 6.4 mg/kg, 8 mg/kg, 9.6 mg/kg, or 12.4 mg/kg; and even more preferably 3.2 mg/kg, 4.8 mg/kg, 6.4 mg/kg, 8 mg/kg, 9.6 mg/kg, or 12.4 mg/kg.

The administration interval of the anti-HER3 antibody-drug conjugate used in the present invention is preferably once a week (q1w), once every two weeks (q2w), once every three weeks (q3w), or once every four weeks (q4w); and more preferably once every three weeks (q3w).

EXAMPLES

The present invention will be described specifically with the examples shown below; however, the invention is not intended to be limited to these. These are not intended to be construed restrictively in any sense.

Example 1: Preparation of an Antibody-Drug Conjugate

According to the production method described in WO 2015/155998, an anti-HER3 antibody comprising a heavy chain consisting of the amino acid sequence represented by SEQ ID NO:9 (FIG. 1) and a light chain consisting of the amino acid sequence represented by SEQ ID NO:10 (FIG. 2) (referred to as "anti-HER3 antibody (1)" in the present invention) was used to produce an anti-HER3 antibody-drug conjugate in which a drug-linker represented by the following formula:

[Formula 10]

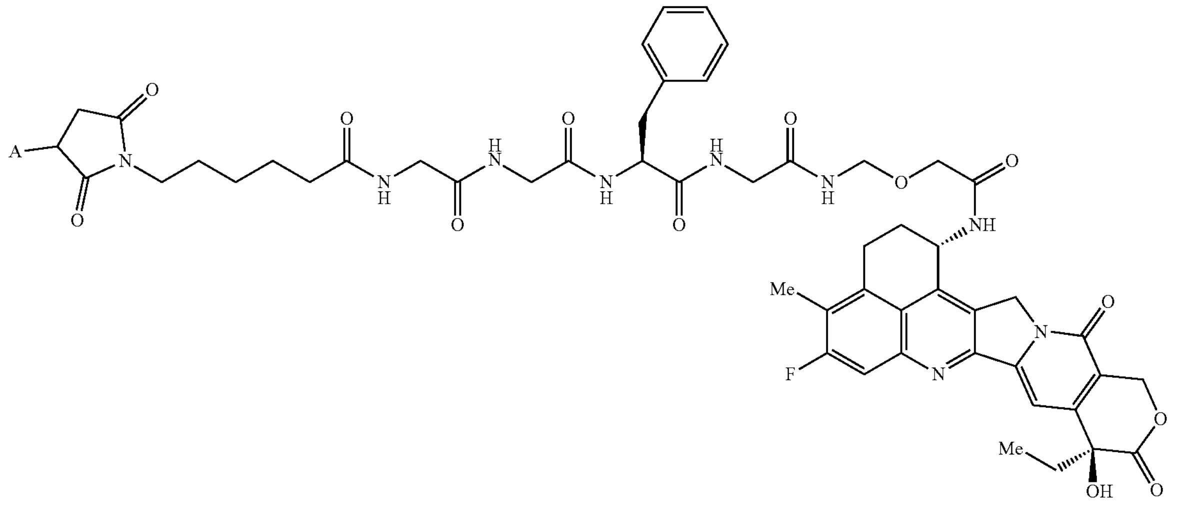

wherein A represents the connecting position to an anti-HER3 antibody, is conjugated to the anti-HER3 antibody via a thioether bond (referred to as "HER3-ADC (1)" in the present invention). The average number of conjugated drug molecules per antibody molecule in HER3-ADC (1) was 7.6.

Example 2: Test on Sensitivity of HER3-ADC (1) to Cell Strain HCC827GR5

Example 2-1: Cell Proliferation Suppressing Activity Against Cell Strain HCC827 and Cell Strain HCC827GR5

Cell strain HCC827 was cultured in RPMI1640 medium (manufactured by Sigma-Aldrich Corp.) containing R10 medium (10% fetal bovine serum and 1% penicillin-streptomycin B (manufactured by Wako Pure Chemical Industries, Ltd.)). Cell strain HCC827GR5 was cultured in a medium obtained by adding gefitinib at a final concentration of 1 μM into the aforementioned medium. It is noted that cell strain HCC827GR5 has been reported not to exhibit strong sensitivity to erlotinib alone therapy or anti-HER3 antibody (1) (the antibody moiety of HER3-ADC (1)) alone therapy (cf. K. Yonesaka et al., Oncogene (2016) 35, 878-886). After cell strain HCC827 and cell strain HCC827GR5 were cultured, the cells were detached by trypsin treatment and then collected. The number of cells in the cell suspension was measured, the cells were suspended in RPMI1640 medium containing 10% fetal bovine serum, and then the suspension was adjusted to have a concentration of 100,000 cells/mL. 50 μL of each cell suspensions was added to each well of SUMILON 96-well plate (manufactured by Sumitomo Bakelite Co., Ltd.) (5,000 cells/well), and culture was carried out. Three days after the initiation of culture, a HER3-ADC (1) dilution dissolved in R10 medium, or R10 medium alone not containing any drug as a negative control was added to the system, and culture was carried out (the final amount of solution was set to 100 μl per well, and the final concentration of the culture fluid was set to 0, 0.0033, 0.01, 0.033, 0.1, 0.33, 1, 3.3, or 10 μg/mL). On the $7^{th}$ day from the initiation of treatment, 50 μL of CellTiter Glo (manufactured by Promega Corp.) was added to each well, and then the culture system was stirred for 2 minutes with a plate mixer. The plate was left to stand for 30 minutes under light-shielded conditions. An aliquot of 120 μL was taken from each well, transferred onto a black microplate, and the luminescence values were measured with a luminometer.

The cell proliferation suppressing activity (% Control) of each drug was determined using the following formula.

% Control=(Average luminescence value in specimen-added wells÷Average luminescence value in negative control wells)×100

The experiment was performed with 6 wells for each group.

The results are shown in FIG. 3. In cell strain HCC827GR5, 41.3%, 40.0%, and 50.0% cell proliferation suppressing activity were observed in the groups added with 10, 3.3, and 1 μg/mL of HER3-ADC (1), respectively. In contrast, in cell strain HCC827, no cell proliferation suppressing activity was observed at a concentration of 3.3 μg/mL or less.

It is revealed from these results that HER3-ADC (1) exhibits cell proliferation suppressing activity against cell strain HCC827GR5.

Example 2-2: Expression of HER3 mRNA in Cell Strain HCC827 and Cell Strain HCC827GR5

1. Preparation of Total RNAs

Total RNAs were prepared using RNeasy Mini Kit (manufactured by Qiagen N.V.). Cell strain HCC827 was cultured in RPMI1640 medium (manufactured by Sigma-Aldrich Corp.) containing R10 medium (10% fetal bovine serum and 1% penicillin-streptomycin B (manufactured by Wako Pure Chemical Industries, Ltd.)). Cell strain HCC827GR5 was cultured in a medium obtained by adding gefitinib at a final concentration of 1 μM into the aforementioned medium. After cell strain HCC827 and cell strain HCC827GR5 were cultured, the cells were detached by trypsin treatment and then collected. The number of cells in the cell suspension was measured, and the cells were suspended in RPMI1640 medium containing 10% fetal bovine serum. 5,000,000 cells of each cell strain were recovered and centrifuged, and then 600 μL Buffer RLT (containing β-mercaptoethanol at a ratio of 100:1) was added thereto. The mixture was stirred for 30 seconds and then stored at −80° C. The solution thus prepared was dissolved and then added to QIAShredder, and centrifugation was performed for 2 minutes at 15,000 rpm. 600 μL of 70% ethanol was added to the extract, and the mixture was stirred. This solution was added to a spin column, and then the mixture was centrifuged for 15 seconds at 12,000 rpm. 80 μL of DNase (+) (70 μL of Buffer RDD and 10 μL of DNase I stock solution) was added to the spin column, the spin column was left to stand for 15 minutes at room temperature, and then 700 μL of Buffer RW was added thereto. Centrifugation was performed for 15 seconds at a speed of 10,000 rpm or higher. The collection tube was replaced, 500 μL of Buffer RPE was added thereto, and the mixture was centrifuged for 15 seconds at a speed of 10,000 rpm or higher. An extract obtained therefrom was discarded. 500 μL of Buffer RPE was added thereto again, and centrifugation was performed for 2 minutes. Subsequently, the tube for collection was replaced, 100 μL of RNase-free water was added to the spin column, and the mixture was left to stand for 5 minutes. Centrifugation was performed for 15 seconds at a speed of 12,000 rpm or higher, and then the total amount of RNAs in the tube for collection was measured.

2. Preparation of cDNAs

Preparation of cDNAs was carried out using High Capacity RNA-to-cDNA Kit (manufactured by Applied Biosystems, Inc.). To a solution prepared with 2× RT Buffer, 20× RT Enzyme Mix, and Nuclease-free H2O, 2 μg of RNAs prepared by the operation described above was added, and thus a total volume of 20 μL of solution was prepared. Centrifugation was performed to remove air bubbles, and then the solution was mounted in a thermal cycler. The solution was caused to react for 60 minutes at 37° C. and for 5 minutes at 95° C., and then was cooled to 4° C., and thereby a reverse transcription reaction was carried out. Thus, cDNAs were prepared.

3. Quantitative PCR Reaction

A quantitative polymerase chain reaction (qPCR) reaction was carried out using MicroAmp Optical 96-well Reaction Plate. 50 ng of cDNAs prepared by the operation described above was added to the plate, and 12.5 μL of Soraris qPCR Master Mix (2×) (manufactured by Thermo Fisher Scientific, Inc.), 12.5 μL of Soraris Primer/Probe set (20×) for mRNA amplification of HER3 (manufactured by Thermo Fisher Scientific, Inc.), and distilled water were added thereto. In order to produce a calibration curve for calculating the amount of mRNAs, similar operations were carried out for 200, 100, and 20 ng of cDNAs produced from human colon cancer HCT116 cells by a similar technique. The plate to which various specimens had been added was mounted in ABI 7900HT (manufactured by Applied Biosystems, Inc.), and the system was caused to react for 15 minutes at 95° C. Subsequently, 60 cycles of reaction at 95°

C. for 15 seconds and at 60° C. for 60 seconds were carried out, and then the system was cooled to 4° C. for 10 minutes. Subsequently, the fluorescence intensity of each well was measured, the amount of PCR products was quantitatively determined, and thereby the amount of mRNAs of each specimen was measured.

The results are shown in FIG. 4. The amount of HER3 mRNAs in cell strain HCC827GR5 was significantly higher than the amount of HER3 mRNAs derived from cell strain HCC827 (student t-test, $p<0.05$).

Example 2-3: Cell Proliferation Suppressing Activity Against Cell Strain HCC827GR5

Cell strain HCC827GR5 was cultured in a medium obtained by adding gefitinib at a final concentration of 1 μM into RPMI1640 medium (manufactured by Sigma-Aldrich Corp.) containing R10 medium (10% fetal bovine serum and 1% penicillin-streptomycin B (manufactured by Wako Pure Chemical Industries, Ltd.)). After cell strain HCC827GR5 was cultured, the cells were detached by trypsin treatment and then collected. The number of cells in the cell suspension was measured, and the cells were suspended in RPMI1640 medium containing 10% fetal bovine serum. The suspension was adjusted to have a concentration of 100,000 cells/mL. 50 μL of each cell suspension was added to each well of SUMILON 96-well plate (manufactured by Sumitomo Bakelite Co., Ltd.) (5,000 cells/well), and culture was carried out. After three days culture, HER3-ADC (1) dilutions dissolved in R10 medium (final concentration in the culture fluid: 0, 0.0033, 0.01, 0.033, 0.1, 0.33, 1, 3.3, and 10 μg/mL), erlotinib dilutions (final concentration in the culture fluid: 0, 0.0033, 0.01, 0.033, 0.1, 0.33, 1, 3.3, and 10 μM), HER3-ADC (1) dilutions dissolved in R10 medium containing erlotinib in a final concentration of 1 μM (final concentration in the culture fluid: 0, 0.0033, 0.01, 0.033, 0.1, 0.33, 1, 3.3, and 10 μg/mL), and as a negative control, R10 medium not containing any drug were added to the culture, the final amount of the culture fluid in each well was adjusted to 100 μL, and culture was carried out. On the $7^{th}$ day from the initiation of treatment, 50 μL of CellTiter Glo (manufactured by Promega Corp.) was added to each well and then the culture system was stirred for 2 minutes with a plate mixer. The plate was left to stand for 30 minutes under light-shielded conditions. An aliquot of 120 μL was taken from each well and was transferred onto a black microplate, and the luminescence values were measured with a luminometer.

The cell proliferation suppressing activity (% Control) of each drug against cell strain HCC827GR5 was determined using the following formula.

% Control=(Average luminescence value in specimen-added wells÷Average luminescence value in negative control wells)×100

The experiment was performed with 6 wells for each group.

The results are shown in FIG. 5. In cell strain HCC827GR5, 41.3%, 40.0%, and 50.0% cell proliferation suppressing activities were observed in the groups added with 10, 3.3, and 1 μg/mL of HER3-ADC (1), respectively. 31.7%, 52.6%, and 69.2% Cell proliferation suppressing activities were observed in the groups added with 10, 3.3, and 1 μg/mL of erlotinib, respectively. On the other hand, 3.1%, 3.2%, and 3.0% cell proliferation suppressing activities were observed in the groups added with combination of 1 μM of erlotinib and 10, 3.3, and 1 μg/mL of HER3-ADC (1), respectively.

These results show that HER3-ADC (1) exhibited high cell proliferation suppressing activity against cell strain HCC827GR5 when used in combination with erlotinib, compared to the cases where the cells were treated with HER3-ADC (1) alone or erlotinib alone.

Example 2-4: Antitumor Effect on Cell Strain HCC827GR5 Transplanted in Nude Mice Cell strain HCC827GR5 was cultured in RPMI1640 medium (manufactured by Sigma-Aldrich Corp.) containing R10 medium (10% fetal bovine serum and 1% penicillin-streptomycin B (manufactured by Wako Pure Chemical Industries, Ltd.)) and erlotinib at a final concentration of 1 μM, subsequently the cells were detached by trypsin treatment and then collected. The number of cells in the cell suspension was measured, and the cells were suspended in R10 medium. The suspension was adjusted to have a concentration of 75,000,000 cells/mL. 100 μL of the cell suspension thus prepared (7,500,000 cells) was transplanted subcutaneously into the ventral region of 6-week old female nude mice (BALB/cAJcl-nu/nu), and then after 7 days from tumor transplantation, at which the average value of the estimated fetal tumor volume of the transplanted tumors became 110 $mm^2$, grouping was carried out. Then, drug administration was initiated (day 0). HER3-ADC (1) was dissolved in phosphate buffer saline (PBS), and the solution was adjusted to have a concentration of 1 mg/mL. Erlotinib was dissolved in a hydroxypropylmethyl cellulose (HPMC) solution, and the solution was adjusted to have a concentration of 2.75 mg/mL. To the single-agent treatment groups of each drug, from day 0 to day 49 at the maximum, prepared HER3-ADC (1) was administered intraperitoneally once a week (7 times in total) at a dose of 200 μL/mouse (10 mg/kg), and prepared erlotinib was administered orally six times a week (19 in total) at a dose of 0.18 mL/mouse (25 mg/kg). On the other hand, to the combination treatment group, HER3-ADC (1) and erlotinib were administered from day 0 at the same dose in the same schedule as those of the single-agent treatment groups. A control group, which was not subjected to administration, was also established. For all of the groups, ten mice were used per group. After the initiation of administration, the tumor diameters (major axis and minor axis) were measured twice a week (on days 0, 3, 7, 10, 14, 17, 21, 24, 28, 31, 35, 38, 41, 45, and 49), and the estimated tumor volumes in each group were calculated according to the following formula. Subsequently, the average value of the estimated tumor volume for each group was calculated.

Estimated tumor volume (Volume, $mm^3$)=major axis (mm)×minor axis $(mm)^2$÷2

Furthermore, the tumor growth inhibition ratio of each group compared with the control group was calculated according to the following formula.

Tumor growth inhibition ratio (%)=100−(average value of estimated tumor volume of treatment group÷average value of estimated tumor volume of control group×100)

From the viewpoint of animal ethics, the measurement for the control and erlotinib single-agent treatment groups was terminated at the $21^{st}$ day since the estimated tumor volume reached 1,200 to 1,500 $mm^3$. Along with this, the calculation of the tumor growth inhibition ratio (%) was made up to day 21.

The results are shown in Table 1, Table 2, and FIG. 6. Erlotinib did not exhibit efficacy against cell strain HCC827GR5. In contrast, significant antitumor effects were observed in the HER3-ADC (1) treatment group and the combined treatment group of HER3-ADC (1) and erlotinib (on Day 21, Dunnet's Multiple Comparison test $p<0.001$).

These results show that HER3-ADC (1) exhibited a significantly high antitumor effect on cell strain HCC827GR5 transplanted in nude mice when used alone or in combination with erlotinib, compared to the case of no treatment or the case of treatment with erlotinib alone (on Day 21, Dunnet's Multiple Comparison test $p<0.001$).

TABLE 1

| Estimated tumor volume | Average value ($mm^3$) | Standard deviation | Average value ($mm^3$) | Standard deviation | Average value ($mm^3$) | Standard deviation |
|---|---|---|---|---|---|---|
| | Day 0 | | Day 3 | | Day 7 | |
| Control group | 127.9 | 45.4 | 243.2 | 83.4 | 469.4 | 181.9 |
| HER3-ADC (1) treatment group | 118.5 | 38.8 | 208.0 | 91.0 | 233.0 | 110.1 |
| Erlotinib treatment group | 124.5 | 42.4 | 189.7 | 105.7 | 347.5 | 171.2 |
| Combination treatment group | 114.5 | 39.3 | 139.5 | 85.6 | 98.7 | 58.1 |
| | Day 10 | | Day 14 | | Day 17 | |
| Control group | 592.1 | 199.6 | 874.8 | 272.9 | 1404.8 | 377.1 |
| HER3-ADC (1) treatment group | 217.0 | 102.4 | 198.0 | 83.0 | 161.5 | 92.5 |
| Erlotinib treatment group | 420.0 | 172.8 | 747.8 | 174.7 | 1117.9 | 334.2 |
| Combination treatment group | 90.0 | 44.6 | 95.6 | 52.8 | 89.0 | 59.6 |
| | Day 21 | | Day 24 | | Day 28 | |
| Control group | 1552.7 | 402.7 | N.A. | N.A. | N.A. | N.A. |
| HER3-ADC (1) treatment group | 203.3 | 142.4 | 217.6 | 168.5 | 309.2 | 233.2 |
| Erlotinib treatment group | 1225.5 | 360.3 | N.A. | N.A. | N.A. | N.A. |
| Combination treatment group | 125.3 | 100.0 | 133.1 | 113.8 | 229.1 | 177.1 |
| | Day 31 | | Day 35 | | Day 38 | |
| Control group | N.A. | N.A. | N.A. | N.A. | N.A. | N.A. |
| HER3-ADC (1) treatment group | 363.4 | 346.4 | 575.1 | 483.6 | 668.0 | 636.0 |
| Erlotinib treatment group | N.A. | N.A. | N.A. | N.A. | N.A. | N.A. |
| Combination treatment group | 331.1 | 253.8 | 372.7 | 300.1 | 491.3 | 345.6 |
| | Day 41 | | Day 45 | | Day 49 | |
| Control group | N.A. | N.A. | N.A. | N.A. | N.A. | N.A. |
| HER3-ADC (1) treatment group | 787.2 | 622.8 | 942.6 | 754.2 | 1092.5 | 887.0 |
| Erlotinib treatment group | N.A. | N.A. | N.A. | N.A. | N.A. | N.A. |
| Combination treatment group | 571.9 | 383.7 | 861.6 | 545.6 | 1074.8 | 660.3 |

N.A.: No measurement was made.

TABLE 2

| Tumor growth inhibition ratio (%) | Day 0 | Day 3 | Day 7 | Day 10 | Day 14 |
|---|---|---|---|---|---|
| HER3-ADC(1) treatment group | 7.4 | 14.5 | 50.7 | 63.3 | 77.4 |
| Erlotinib treatment group | 2.7 | 22.0 | 26.0 | 29.1 | 14.5 |
| Combination treatment group | 10.5 | 42.6 | 79.0 | 84.8 | 89.1 |

TABLE 2-continued

| Tumor growth inhibition ratio (%) | Day 17 | Day 21 |
|---|---|---|
| HER3-ADC(1) treatment group | 88.5 | 86.9 |
| Erlotinib treatment group | 20.4 | 21.1 |
| Combination treatment group | 93.7 | 91.9 |

From the results of Example 2, the antitumor effect of HER3-ADC (1) on cell strain HCC827GR5 was confirmed. Cell strain HCC827GR5 is a cell strain derived from HCC827, which is a cell strain of human non-small cell lung cancer, and has acquired resistance to EGFR-TKI, and is a cell strain corresponding to EGFR T790M mutation-negative non-small cell lung cancer.

It has been thereby shown that administration of an anti-HER3 antibody-drug conjugate can provide a therapeutic agent and a therapeutic method for EGFR-TKI resistant and EGFR T790M mutation-negative non-small cell lung cancer.

Example 3: Test on Sensitivity of HER3-ADC (1) to Cell Strain PC9 and Cell Strain PC9AZDR7

Example 3-1: Production of Osimertinib-Resistant Cell Strain PC9

PC9, a non-small cell lung cancer strain, was cultured in RPMI-1640 medium (manufactured by Sigma-Aldrich Corp.) containing 10% fetal bovine serum and 1% penicillin-streptomycin B (manufactured by Wako Pure Chemical Industries, Ltd.). After 1 nM osimertinib was added into the culture fluid, culture was started, and passage culture was carried out by increasing the concentration of added osimertinib in a stepwise manner. Finally, osimertinib-resistant cell strain PC9 (PC9AZDR7) was established by culturing the cells in a medium containing 100 nM osimertinib.

Example 3-2: Cell Proliferation Suppressing Activity Against Cell Strains PC9 and PC9AZDR7

Cell strains PC9 and PC9AZDR7 were cultured in RPMI1640 medium (manufactured by Sigma-Aldrich Corp.) containing 10% fetal bovine serum and 1% penicillin-streptomycin B (manufactured by Wako Pure Chemical Industries, Ltd.). PC9AZDR7 was cultured with 100 nM osimertinib added to the medium. After cell strains PC9 and PC9AZDR7 were cultured, the cells were detached by trypsin treatment and then collected. The numbers of cells in the cell suspensions were measured, and the cells were respectively suspended in RPMI1640 medium containing 2% fetal bovine serum. Subsequently, 50 μL of each cell suspension was added into each well of SUMILON 96-well plate (manufactured by Sumitomo Bakelite Co., Ltd.) (10,000 cells/well), and culture was carried out. One day after the initiation of culture, osimertinib dilutions, each of which was prepared to have one of various concentrations, or as a negative control, RPMI-1640 medium not containing any drug was added, and culture was carried out. The final concentrations of osimertinib were set at 0, 0.001, 0.0033, 0.01, 0.033, 0.1, 0.33, 1, and 3.3 μM. On the $3^{rd}$ day from the initiation of treatment, 50 μL of CellTiter Glo (manufactured by Promega Corp.) was added to each well, and then the culture system was stirred for 2 minutes with a plate mixer. The plate was left to stand for 30 minutes under light-shielded conditions. An aliquot of 120 μL was taken from each well and was transferred onto a black microplate, and the luminescence values were measured with a luminometer.

The cell proliferation suppressing activity (% of control) of each drug was calculated using the following formula.

% of Control=(Average luminescence value in specimen-added wells÷average luminescence value in negative control wells)×100

The experiment was performed with 6 wells for each group.

The results are shown in FIG. 7. Strong cell proliferation suppressing activities were observed in the groups receiving 0.01 μM or higher concentrations of osimertinib added to cell strain PC9. In contract, no cell proliferation suppressing activity was observed when 1 μM or lower concentrations of osimertinib were added to cell strain PC9AZDR7.

It was revealed from these results that PC9AZDR7 exhibits its drug resistance to osimertinib.

Example 3-3: Expression of HER3 Proteins in Cell Strain PC9 and Cell Strain PC9AZDR7

Expression of HER3 proteins in cell strains PC9 and PC9AZDR7 was measured using QIFIKIT (manufactured by Dako Corp.). After PC9 and PC9AZDR7 were cultured, an anti-human murine HER3 antibody (Clone 1B4C3, manufactured by Dako Corp.) or a mouse IgG2a isotype control antibody was added and the cells were cultured. The cells were further cultured with FITC composite anti-mouse IgG antibody (manufactured by Dako Corp.). The fluorescence intensity of each specimen was measured using LSR-Fortessa X-20 (manufactured by BD Biosciences, Inc.), and thereby the HER3 protein expression level in each cell strain was measured.

The results are shown in FIG. 8. The HER3 protein expression level in PC9 was 5,088 molecules/cell, and the expression level in PC9AZDR7 was 15,469 molecules/cell. Thus, three times higher HER3 protein expression level was observed in PC9AZDR7 than in PC9 (unpaired T test, $p<0.001$).

It was revealed from these results that the HER3 protein expression level in PC9AZDR7, which has been established from non-small cell lung cancer strain PC9 and exhibits resistance to osimertinib, is markedly higher than that in the parental strain PC9.

Example 3-4: Antitumor Effect of HER3-ADC (1) on Cell Strains PC9 and PC9AZDR7 Transplanted in Nude Mice Cell strains PC9 and PC9AZDR7 were cultured in RPMI1640 medium (manufactured by Sigma-Aldrich Corp.) containing 10% fetal bovine serum and 1% penicillin-streptomycin B (manufactured by Wako Pure Chemical Industries, Ltd.). Cell strain PC9AZDR7 was cultured in a medium containing osimertinib at a final concentration of 100 nM. After culturing, the cells were detached by trypsin treatment and then collected. The number of cells in the cell suspensions was measured, and the respective cell suspensions were prepared. 100 μL of each cell suspension thus prepared (5,000,000 cells) was transplanted subcutaneously into the ventral region of 6-week old female nude mice (BALB/cAJcl-nu/nu), and then at a time point when the average value of the estimated tumor volume of the transplanted tumors became about 200 $mm^2$, grouping was carried out. Then, drug administration was initiated (day 0). HER3-ADC (1) was dissolved in phosphate buffer saline (PBS), and the solution was adjusted to have a concentration of 0.6 mg/mL. HER3-ADC (1) thus prepared was intraperitoneally administered once at a dose of 100 μL/mouse (3 mg/kg) on Day 0. As a control group, a group administered with PBS only was established. Eight mice were used for the control group, and nine mice were used for the HER3-ADC (1) group. After the initiation of administration, the tumor diameters (major axis and minor axis) were measured twice a week, and the estimated tumor volume in each group was calculated according to the following formula. Subsequently, the average value of the estimated tumor volume for each group was calculated.

Estimated tumor volume (Volume, $mm^3$)=major axis (mm)×minor axis $(mm)^2$÷2

The tumor growth inhibition ratio of each group compared with the control group was calculated using the following formula.

Tumor growth inhibition ratio (%)=100−(average value of estimated tumor volume of treatment group÷average value of estimated tumor volume of control group×100)

The antitumor effect of HER3-ADC (1) on cell strain PC9 is shown in Table 3 and FIG. 9, and the antitumor effect of HER3-ADC (1) on cell strain PC9AZDR7 is shown in Table 4 and FIG. 10. HER3-ADC (1) did not exhibit efficacy against cell strain PC9 (tumor growth inhibition ratio on Day 21: 17%). In contrast, a significant antitumor effect (tumor growth inhibition ratio on Day 18: 72%) was observed in the HER3-ADC (1) treatment group against PC9AZDR7 (on Day 18, unpaired t test $p<0.05$).

TABLE 3

| Estimated tumor volume | Average value (mm$^3$) | Standard deviation | Average value (mm$^3$) | Standard deviation | Average value (mm$^3$) | Standard deviation |
|---|---|---|---|---|---|---|
| | Day 0 | | Day 3 | | Day 7 | |
| Control group | 192.6 | 76.1 | 335.4 | 136.1 | 411.2 | 220.5 |
| HER3-ADC (1) treatment group | 251.1 | 154.1 | 492.6 | 308.6 | 513.1 | 375.1 |
| | Day 10 | | Day 15 | | Day 18 | |
| Control group | 488.6 | 251.4 | 762.8 | 397.2 | 938.4 | 541 |
| HER3-ADC (1) treatment group | 603.4 | 590 | 826.2 | 855.3 | 1080.7 | 1098.3 |
| | Day 21 | | Day 24 | | Day 28 | |
| Control group | 1343.2 | 727.6 | 1774.7 | 1122.6 | 1222.2 | 616.2 |
| HER3-ADC (1) treatment group | 1115.9 | 1202.4 | 1447.7 | 1618.5 | 1791.3 | 1968 |

TABLE 4

| Estimated tumor volume | Average value (mm$^3$) | Standard deviation | Average value (mm$^3$) | Standard deviation | Average value (mm$^3$) | Standard deviation |
|---|---|---|---|---|---|---|
| | Day 0 | | Day 3 | | Day 7 | |
| Control group | 287.1 | 172.3 | 461.3 | 296 | 845.6 | 448 |
| HER3-ADC (1) treatment group | 249.3 | 159.1 | 250.7 | 123.7 | 286.8 | 200.7 |
| | Day 10 | | Day 15 | | Day 18 | |
| Control group | 1061.4 | 557.2 | 1391.1 | 766.7 | 2013.4 | 1412.6 |
| HER3-ADC (1) treatment group | 333.9 | 174.9 | 472.3 | 284 | 558.3 | 387.2 |
| | Day 21 | | Day 24 | | Day 28 | |
| Control group | 2115.9 | 1245.5 | 2111.6 | 888.7 | 2260.7 | 1260 |
| HER3-ADC (1) treatment group | 716.9 | 576.4 | 954.1 | 828.5 | 1000.9 | 825.1 |

It was revealed from these results that HER3-ADC (1) exhibits a significantly higher antitumor effect on cell strain PC9AZDR7 transplanted in nude mice than the control group.

It was therefore demonstrated that a therapeutic agent and a therapeutic method for osimertinib-resistant non-small cell lung cancer may be provided by administering an anti-HER3 antibody-drug conjugate.

Example 3-5: Antitumor Effect of Combination of HER3-ADC (1) and Osimertinib on Cell Strain PC9AZDR7 Transplanted in Nude Mice Cell strain PC9AZDR7 was cultured in RPMI1640 medium (manufactured by Sigma-Aldrich Corp.) containing 10% fetal bovine serum and 1% penicillin-streptomycin B (manufactured by Wako Pure Chemical Industries, Ltd.) and 100 nM osimertinib. After cell strain PC9AZDR7 was cultured, the cells were detached by trypsin treatment and then collected. The number of cells in the cell suspension was measured, and the respective cell suspensions were prepared. 100 μL of each cell suspension thus prepared (34,000,000 cells) was transplanted subcutaneously into the ventral region of 6-week old female nude mice (BALB/cAJcl-nu/nu), and then at a time point when the average value of the estimated tumor volume of the transplanted tumors became about 60 mm$^2$, grouping was carried out (day 0). From the next day of grouping (1$^{st}$ day), drug administration was initiated. HER3-ADC (1) was dissolved in phosphate buffer saline (PBS), and the solution was adjusted to have a concentration of 0.1 mg/mL. Osimertinib was dissolved in distilled water for injection containing 0.1% dimethyl sulfoxide and 30% polyethylene glycol 300, and the solution was adjusted to have a concentration of 0.2 mg/mL. In the single agent-treatment group of each drug, HER3-ADC (1) was intraperitoneally administered on Day 1 at a dose of 200 μL/mouse (1 mg/kg), and osimertinib was orally administered on Days 1, 2, 3, 4, 5, 8, 9, 10, 11, 12, 15, 16, 17, 18, and 19 at a dose of 100 μL/mouse (1 mg/kg). In the combination treatment group of HER3-ADC (1) and osimertinib, each drug was administered at the same amounts in the same administration schedule as those in the respective single agent-treatment groups. As a control group, a group not receiving any administration was established. Eleven mice were used for the control group, twelve mice were used for the HER3-ADC (1) single agent group, twelve mice were used for the osimertinib single agent group, and ten mice were used for the combination group of HER3-ADC (1) and osimertinib. After the initiation of administration, the tumor diameters (major axis and minor axis) were measured twice a week, and the estimated tumor volume in each group was calculated according to the following formula. Subsequently, the average value of the estimated tumor volume for each group was calculated.

Estimated tumor volume (Volume, $mm^3$)=major axis (mm)×minor axis $(mm)^2$÷2

The tumor growth inhibition ratio of each group compared with the control group was calculated using the following formula.

Tumor growth inhibition ratio (%)=100−(average value of estimated tumor volume of treatment group÷average value of estimated tumor volume of control group×100)

The results are shown in Table 5 and FIG. 11. neither the single-agent treatment group with 1 mg/kg of HER3-ADC (1) nor the single-agent treatment group with 1 mg/kg of osimertinib exhibited high efficacy against cell strain PC9AZDR7 (tumor proliferation inhibition ratio on Day 21: HER3-ADC (1), 25.3%, osimertinib, 27.7%). In contrast, a significant antitumor effect (tumor proliferation inhibition ratio on Day 21: 66.6%; on Day 21, p=0.0057 in respect to the HER3-ADC (1) single-agent treatment group, p=0.0092 in respect to the osimertinib single-agent treatment group, Dunnett's test) was observed in the combination treatment group of 1 mg/kg of HER3-ADC (1) and 1 mg/kg of osimertinib.

TABLE 5

| Estimated tumor volume | Average value ($mm^3$) | Standard deviation | Average value ($mm^3$) | Standard deviation | Average value ($mm^3$) | Standard deviation |
|---|---|---|---|---|---|---|
| | Day 0 | | Day 5 | | Day 8 | |
| Control group | 67.8 | 38.0 | 265.1 | 134.3 | 288.4 | 151.3 |
| HER3-ADC (1) treatment group | 60.4 | 27.2 | 264.5 | 115.8 | 266.5 | 129.5 |
| Osimertinib treatment group | 64.2 | 30.2 | 249.3 | 79.8 | 271.7 | 96.3 |
| Combination treatment group | 56.9 | 25.3 | 132.8 | 116.8 | 134.3 | 84.7 |
| | Day 11 | | Day 16 | | Day 18 | |
| Control group | 435.0 | 209.7 | 571.8 | 269.5 | 721.2 | 331.0 |
| HER3-ADC (1) treatment group | 337.0 | 148.2 | 488.6 | 198.6 | 665.2 | 232.2 |
| Osimertinib treatment group | 357.2 | 105.9 | 533.4 | 217.0 | 650.7 | 239.6 |
| Combination treatment group | 141.5 | 88.8 | 215.9 | 160.0 | 299.0 | 187.2 |

| Estimated tumor volume | Day 21 Average value ($mm^3$) | Standard deviation |
|---|---|---|
| Control group | 982.7 | 566.7 |
| HER3-ADC (1) treatment group | 733.9 | 237.7 |
| Osimertinib treatment group | 710.6 | 357.8 |
| Combination treatment group | 328.6 | 217.3 |

TABLE 6

| Tumor growth inhibition ratio (%) | Day 0 | Day 5 | Day 8 | Day 11 | Day 16 | Day 18 | Day 21 |
|---|---|---|---|---|---|---|---|
| HER3-ADC (1) treatment group | 10.9 | 0.2 | 7.6 | 22.5 | 14.5 | 7.8 | 25.3 |
| Osimertinib treatment group | 5.3 | 6.0 | 5.8 | 17.9 | 6.7 | 9.8 | 27.7 |
| Combination treatment group | 16.1 | 49.9 | 53.4 | 67.5 | 62.2 | 58.5 | 66.6 |

It has been revealed from these results that the combination therapy of HER3-ADC (1) and osimertinib exhibits a significantly higher antitumor effect on cell strain PC9AZDR7 transplanted in nude mice, than the single agent-therapy with HER3-ADC (1) alone or osimertinib alone.

Sequence Free Text

SEQ ID NO:1: Amino acid sequence of CDRH1 of anti-HER3 antibody (1)
SEQ ID NO:2: Amino acid sequence of CDRH2 of anti-HER3 antibody (1)
SEQ ID NO:3: Amino acid sequence of CDRH3 of anti-HER3 antibody (1)
SEQ ID NO:4: Amino acid sequence of CDRL1 of anti-HER3 antibody (1)
SEQ ID NO:5: Amino acid sequence of CDRL2 of anti-HER3 antibody (1)
SEQ ID NO:6: Amino acid sequence of CDRL3 of anti-HER3 antibody (1)
SEQ ID NO:7: Amino acid sequence of a heavy chain variable region of anti-HER3 antibody (1)
SEQ ID NO:8: Amino acid sequence of a light chain variable region of anti-HER3 antibody (1)
SEQ ID NO:9: Amino acid sequence of a heavy chain of anti-HER3 antibody (1)
SEQ ID NO:10: Amino acid sequence of a light chain of anti-HER3 antibody (1)

The invention claimed is:

1. A therapeutic method for osimertinib-resistant non-small cell lung cancer, comprising administering an anti-HER3 antibody-drug conjugate to a human subject in need thereof.

2. The therapeutic method according to claim 1, wherein the non-small cell lung cancer is EGFR T790M mutation-negative non-small cell lung cancer.

3. The therapeutic method according to claim 2, wherein the osimertinib-resistant non-small cell lung cancer is further resistant to gefitinib, erlotinib or afatinib.

4. The therapeutic method according to claim 2, wherein the osimertinib-resistant non-small cell lung cancer is further resistant to gefitinib or erlotinib.

5. The therapeutic method according to claim 1, wherein the osimertinib-resistant non-small cell lung cancer is further resistant to gefitinib, erlotinib, afatinib, or a combination thereof.

6. The therapeutic method according to claim 1, wherein the non-small cell lung cancer expresses HER3.

7. The therapeutic method according to claim 1, wherein the anti-HER3 antibody-drug conjugate is an anti-HER3 antibody-drug conjugate in which a drug-linker represented by the following formula:

9. The therapeutic method according to claim 1, wherein the anti-HER3 antibody is an antibody comprising a heavy chain comprising a heavy chain variable region consisting of the amino acid sequence represented by SEQ ID NO:7, and a light chain comprising a light chain variable region consisting of the amino acid sequence represented by SEQ ID NO:8.

10. The therapeutic method according to claim 1, wherein the anti-HER3 antibody is an antibody comprising a heavy chain consisting of the amino acid sequence represented by SEQ ID NO:9, and a light chain consisting of the amino acid sequence represented by SEQ ID NO:10.

11. The therapeutic method according to claim 10, wherein the anti-HER3 antibody lacks a lysine residue at the carboxyl terminus of the heavy chain.

12. The therapeutic method according to claim 1, wherein the average number of units of the drug-linker conjugated per antibody molecule in the anti-HER3 antibody-drug conjugate is in the range of 7 to 8.

13. The therapeutic method according to claim 1, wherein the average number of units of the drug-linker conjugated per antibody molecule in the anti-HER3 antibody-drug conjugate is in the range of 7.5 to 8.

[Formula 2]

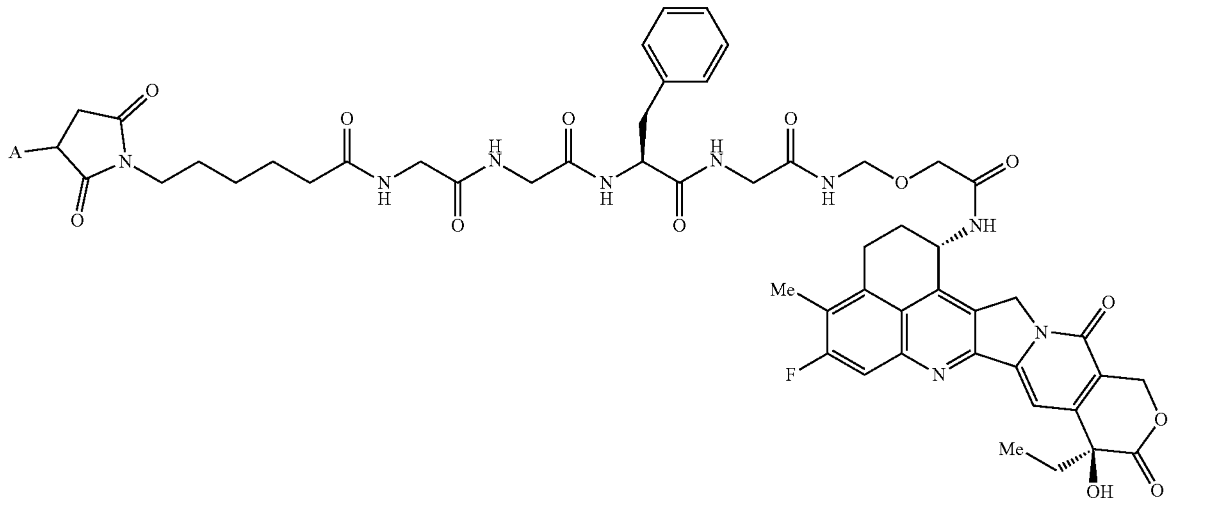

wherein A represents the connecting position to an anti-HER3 antibody, is conjugated to the anti-HER3 antibody via a thioether bond.

8. The therapeutic method according to claim 1, wherein the anti-HER3 antibody is an antibody comprising a heavy chain comprising CDRH1 consisting of the amino acid sequence represented by SEQ ID NO:1, CDRH2 consisting of the amino acid sequence represented by SEQ ID NO:2, and CDRH3 consisting of the amino acid sequence represented by SEQ ID NO:3, and a light chain comprising CDRL1 consisting of the amino acid sequence represented by SEQ ID NO:4, CDRL2 consisting of the amino acid sequence represented by SEQ ID NO:5, and CDRL3 consisting of the amino acid sequence represented by SEQ ID NO:6.

14. The therapeutic method according to claim 1, wherein the anti-HER3 antibody-drug conjugate is administered in combination with a second drug.

15. The therapeutic method according to claim 14, wherein the second drug is gefitinib, erlotinib, afatinib, or osimertinib.

16. The therapeutic method according to claim 15, wherein the second drug is erlotinib.

17. The therapeutic method according to claim 15, wherein the second drug is osimertinib.

18. The therapeutic method according to claim 1, wherein the anti-HER3 antibody-drug conjugate comprises a drug-linker conjugated to an antibody via a thioether bond, wherein the antibody-drug conjugate releases a drug having a structure of:

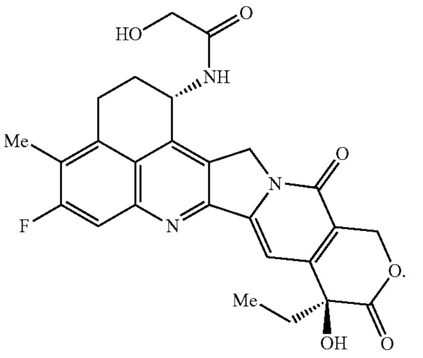 [SMILES: CC[C@@]1(O)C(=O)OCc2c1cc1n(c2=O)Cc2c-1nc1cc(F)c(C)c3c1c2[C@@H](NC(=O)CO)CC3]
19. The therapeutic method according to claim 18, wherein the anti-HER3 antibody-drug conjugate is administered in combination with a second drug.
20. The therapeutic method according to claim 19, wherein the second drug is gefitinib, erlotinib, afatinib, or osimertinib.
21. The therapeutic method according to claim 20, wherein the second drug is osimertinib.
* * * * *